United States Patent
Mashima et al.

(10) Patent No.: US 11,377,415 B2
(45) Date of Patent: Jul. 5, 2022

(54) METHOD FOR CONVERTING N,N-DIALKYLAMIDE COMPOUND INTO ESTER COMPOUND USING COMPLEX OF FOURTH-PERIOD TRANSITION METAL AS CATALYST

(71) Applicants: TAKASAGO INTERNATIONAL CORPORATION, Tokyo (JP); OSAKA UNIVERSITY, Osaka (JP)

(72) Inventors: Kazushi Mashima, Osaka (JP); Haruki Nagae, Osaka (JP); Takahiro Hirai, Osaka (JP); Daiki Kato, Osaka (JP); Shusei Soma, Osaka (JP); Shinya Akebi, Osaka (JP); Shoko Akiyama, Osaka (JP); Kazuhiko Matsumura, Kanagawa (JP); Yoshimasa Matsushima, Tokyo (JP)

(73) Assignees: TAKASAGO INTERNATIONAL CORPORATION, Tokyo (JP); OSAKA UNIVERSITY, Osaka (JP)

( * ) Notice: Subject to any disclaimer, the term of this patent is extended or adjusted under 35 U.S.C. 154(b) by 0 days.

(21) Appl. No.: 16/976,025

(22) PCT Filed: Feb. 28, 2019

(86) PCT No.: PCT/JP2019/007961
§ 371 (c)(1),
(2) Date: Aug. 26, 2020

(87) PCT Pub. No.: WO2019/168135
PCT Pub. Date: Sep. 6, 2019

(65) Prior Publication Data
US 2020/0399200 A1    Dec. 24, 2020

(30) Foreign Application Priority Data

Feb. 28, 2018   (JP) .............................. JP2018-035579
Jun. 18, 2018   (JP) .............................. JP2018-115565

(51) Int. Cl.
  *C07C 67/20*    (2006.01)
  *C07F 9/00*     (2006.01)
  (Continued)

(52) U.S. Cl.
  CPC ............... *C07C 67/20* (2013.01); *B01J 31/12* (2013.01); *B01J 31/22* (2013.01); *C07F 9/005* (2013.01); *C07F 9/50* (2013.01); *B01J 31/24* (2013.01)

(58) Field of Classification Search
  CPC .......... C07F 13/005; C07F 9/50; C07F 9/005; C07C 67/20
  See application file for complete search history.

(56) References Cited

U.S. PATENT DOCUMENTS 6,310,236 B1    10/2001    Nakamura et al.
2003/0032743 A1*  2/2003   Fujisawa ................ C08F 10/00
                                                        526/131

(Continued)

FOREIGN PATENT DOCUMENTS

EP    3124114 A1    2/2017
JP    55-143935 A   11/1980
(Continued)

OTHER PUBLICATIONS

STN 05 2008 one page (Year: 2008).*
(Continued)

*Primary Examiner* — Caixia Lu
(74) *Attorney, Agent, or Firm* — Sughrue Mion, PLLC

(57) ABSTRACT

A method for converting an N,N-dialkylamide compound into an ester compound includes using a fourth period transition metal complex as a catalyst. The fourth period transition metal complex is obtained by a reaction of a
(Continued)

precursor having a fourth period transition metal with a nitrogen-containing compound or a phosphorus-containing compound.

3 Claims, 5 Drawing Sheets

(51) Int. Cl.

| | | |
|---|---|---|
| *C07F 9/50* | (2006.01) | |
| *B01J 31/22* | (2006.01) | |
| *B01J 31/12* | (2006.01) | |
| *B01J 31/24* | (2006.01) | |

(56) References Cited

U.S. PATENT DOCUMENTS

| | | |
|---|---|---|
| 2012/0263974 A1 | 10/2012 | Menozzi et al. |
| 2017/0275241 A1 | 9/2017 | Ohshima et al. |

FOREIGN PATENT DOCUMENTS

| | | |
|---|---|---|
| JP | 11-292824 A | 10/1999 |
| JP | 2008-37835 A | 2/2008 |
| JP | 2013-512978 A | 4/2013 |
| JP | 2013-177522 A | 9/2013 |
| JP | 2014-159546 A | 9/2014 |
| WO | 2015/146294 A1 | 10/2015 |

OTHER PUBLICATIONS

International Search Report (PCT/ISA/210) issued by the International Searching Authority in International Application No. PCT/JP2019/007961, dated May 28, 2019.
Written Opinion (PCT/ISA/237) issued by the International Searching Authority in International Application No. PCT/JP2019/007961, dated May 28, 2019.
Lawrence E. Fisher et al., "Mild hydrolysis or alcoholysis of amides. Ti(IV) catalyzed conversion of primary carboxamides to carboxylic acids or esters[1,2]", Can. J. Chem., 1994, vol. 72, pp. 142-145 (4 pages total).
Benjamin N. Atkinson et al., "Scandium triflate catalyzed ester synthesis using primary amides", Tetrahedron Letters, Oct. 28, 2014, vol. 55, pp. 6935-6938 (4 pages total).
S.M.A. Hakim Siddiki et al., "Versatile and sustainable alcoholysis of amides by a reusable $CeO_2$ catalyst", Royal Society of Chemistry, 2014, vol. 4, pp. 35803-35807 (5 pages total).
Yusuke Kita et al., "Zinc-Catalyzed Amide Cleavage and Esterification of β-Hydroxyethylamides**", Angewandte Communications, 2012, vol. 51, pp. 5723-5726 (4 pages total).
Toru Deguchi et al., "Direct Catalytic Alcoholysis of Unactivated 8-Aminoquinoline Amides", ACS Catalysis, Mar. 28, 2017, pp. 3157-3161 (5 pages total).
Liana Hie et al., "Conversion of amides to esters by the nickel-catalysed activation of amide C-N bonds", Nature, Aug. 2015. Vol. 524, pp. 79-83 (5 pages total).
Tadeusz Glowiak et al., "Molecular structure and spectral properties of mono- and dinuclear complexes formed by manganese (II), 2,6-dimethoxybenzoate and 2,2' -bipyridine or 2-methylpyrazine", Inorganica Chimica Acta, 1995, vol. 236, No. 1-2, pp. 149-154 (6 pages total).
Eugenio Garribba et al., "Monomeric versus dimeric structures in ternary complexes of manganese(II) with derivatives of benzoic acid and nitrogenous bases: structural details and spectral properties", Inorganica Chimica Acta, 2004, vol. 357, No. 7, pp. 2038-2048 (11 pages total).
Abhilasha Mohan Baruah et al., "Manganese and Cadmium Benzoate Complexes Having 8-Aminoquinoline Ancillary Ligand", The Open Inorganic Chemistry Journal, 2008, vol. 2, pp. 62-68 (7 pages total).
Communication dated Sep. 20, 2021 issued by the European Patent Office in EP application No. 19761438.1.
Nagae, H., et al., "Dinuclear manganese alkoxide complexes as catalysts for C-N bond cleavage of simple tertiary N,N-dialkylamides to give esters", Chemical Science, vol. 10, No. 10, Jan. 29, 2019, pp. 2860-2868, XP055839362.
Nishii, Y., et al., "Manganese(II)-Catalyzed Esterification of N-β-Hydroxyethyl-amides", SYNLETT, vol. 26, No. 13, Jan. 1, 2015, pp. 1831-1834, retrieved from https://www.thieme-connect.de/products/ejournals/pdf/10.1055/s-0034-1380428.pdf, XP055839372.
Liu, D., et al., "Carbon-Centered Radical Addition to O=C of Amides or Esters as a Route to C-O Bond Formations", Chemistry-A European Journal, vol. 20, No. 47, Nov. 17, 2014, pp. 15605-15610, XP055839363.
Sain, S., et al., "Two new supramolecular malonato complexes of manganese(II): synthesis, crystal structure and magnetic property", Inorganica Chimica ACTA, vol. 351, Jul. 1, 2003, pp. 12-20, XP055839360.
Mercati, G., et al., "Chelate Complexes of Manganese(II): Synthesis, Spectroscopic and Electron Paramagnetic Resonance Properties of Manganese(II) β-Diketonate Derivatives", Inorganica Chimica Acta, vol. 37, Jan. 1, 1979, pp. 161-168, XP055839361.
Horikawa, R., et al., "μ-Oxo-Dinuclear-Iron(III)-Catalyzed O-Selective Acylation of Aliphatic and Aromatic Amino Alcohols and Transesterification of Tertiary Alcohols", Chemistry-A European Journal, vol. 22, No. 35, Aug. 22, 2016, pp. 12278-12281, XP055839365.
Jain, S., et al., "Synthesis and X-ray crystal structures of [pyH][Fe(pic)$_2$Cl$_2$] and [Fe$_2$(μ$_2$-OMe)$_2$(pic)$_4$] (Hpic=2-picolinic acid)", Inorganic Chemistry Communications, vol. 7, No. 3, 2004, pp. 423-425, XP085036562.
Hayashi, Y., et al., "Enzyme-Like Catalysis via Ternary Complex Mechanism Alkoxy-Bridged Dinuclear Cobalt Complex Mediates Chemoselective O-Esterification over N-Amidation", Journal of the American Chemical Society, vol. 135, No. 16, Apr. 24, 2013, pp. 6192-6199, XP055839369.
Edulji, S., et al., "Catalytic Olefin Cyclopropanation Using μ-Oxo-bis[(salen)iron(III)] Complexes", Organometallics, American Chemical Society, vol. 22, No. 17, Aug. 18, 2003, pp. 3374-3381, XP-001170147.

* cited by examiner

METHOD FOR CONVERTING N,N-DIALKYLAMIDE COMPOUND INTO ESTER COMPOUND USING COMPLEX OF FOURTH-PERIOD TRANSITION METAL AS CATALYST

CROSS-REFERENCE TO RELATED APPLICATIONS

This application is a U.S. National Stage of International Application No. PCT/JP2019/007961, filed on Feb. 28, 2019, which claims priority to Japanese Patent Application No. 2018-035579 filed on Feb. 28, 2018 and Japanese Patent Application No. 2018-115565, filed on Jun. 18, 2018, the entire contents of which are incorporated by reference herein.

TECHNICAL FIELD

The present invention relates to a method for producing an ester compound from an N,N-dialkylamide compound in the presence of an alcohol, using a fourth period transition metal complex as a catalyst.

In addition, the present invention relates to a fourth period transition metal complex, a μ-oxo dimer complex, a method for producing an amidated compound by allowing an amine to react with a carboxylic acid ester, and a method for causing a transesterification reaction.

BACKGROUND ART

Amide bonds are widely found in natural products, physiologically active substances, functional molecules, and the like. It is common that a compound having amide bonds has a very high chemical and thermal stability, as compared with other carboxylic acid derivatives. In addition, amide bonds are a bonding mode that can be used as a protecting group of a carbonyl group or an orientation group in organic synthetic chemistry, and developments of an efficient conversion reaction of an amide compound are desired.

In an organism, cleavage of a specific amide bond (a peptide bond) is performed for cell function control or protein degradation. This cleavage may proceed under mild conditions (temperature around body temperature, and conditions close to neutrality) using a protease in a living body as a catalyst.

On the other hand, as a method in the organic synthetic chemistry, cleavage of an unactivated amide bond is generally difficult due to the high stability of the unactivated amide bond, and it is necessary to react for a long time under severe conditions, such as a strong acid or a strong base, and a high temperature, for the cleavage of the amide bond. In addition, it has been commonly considered difficult to carry out an esterification reaction under neutral conditions by activating a carbon-nitrogen bond of an amide with a transition metal catalyst.

In recent years, a conversion reaction of amide compounds, which uses the fourth period transition metal (first transition metal, 3d transition element) in the long-period periodic table, has been actively studied as a method in synthetic chemistry.

Non-Patent Literature 1 reports that an ester compound can be obtained by allowing a secondary amide compound to react at a high temperature of 200° C. or higher in the presence of an alcohol, using titanium chloride as a catalyst.

Non-Patent Literatures 2 and 3 report that a primary amide compound can be converted into an ester in the presence of an alcohol, using $Sc(OTf)_3$ and $CeO_2$.

Non-Patent Literature 4 reports that an amide compound having an N-β-hydroxyethyl group is efficiently esterified via N,O-acyl transfer in an esterification reaction of amide compounds.

Non-Patent Literature 5 reports a reaction of obtaining an ester compound from 8-aminoquinoline amide, which is a secondary amide, by using a nickel complex $Ni(dpm)_2$.

All Non-Patent Literatures describe methods for converting a primary or secondary amide into an ester compound, and these methods were difficult to be applied to a conversion reaction from a tertiary amide to an ester compound.

However, recently, Non-Patent Literature 6 has first reported a transesterification reaction of a tertiary amide using a nickel carbene complex.

CITATION LIST

Non Patent Literature

Non-patent Literature 1: Can. J. Chem. 72 (1994) p. 142
Non-Patent Literature 2: Tetrahedron Lett. 55 (2014) p. 6935
Non-patent Literature 3: RSC Adv 4 (2014) p. 35803
Non-Patent Literature 4: Angew. Chem., Int Ed 51 (2012) p. 5723
Non-Patent Literature 5: ACS Catal. 7 (2017) p. 3157
Non-Patent Literature 6: Nature 524 (2015) p. 79

SUMMARY OF INVENTION

Technical Problem

However, the tertiary amide, which can be converted into an ester compound in Non-Patent Literature 6, is only an N-methyl-N-phenylamide compound, and an ester compound cannot be obtained from a more bulky and "inert" N,N-dialkylamide compound. In addition, since the nickel carbene complex used as a catalyst is unstable and highly toxic, it is not practical.

In this way, a catalytically efficient reaction of converting an N,N-dialkylamide, which is an "inert" tertiary amide compound, into an ester under neutral conditions has not yet been reported.

An object of the present invention is to provide an efficient catalytic reaction of converting an N,N-dialkylamide, which is generally inert to reactions, into an ester compound under neutral conditions, and a metal complex using the fourth period transition metal, which is used as a catalyst in the reaction.

Solution to Problem

As a result of intensive studies to solve the above problems, the present inventors have found out that an N,N-dialkylamide compound can be efficiently converted into an ester compound under mild conditions by adding, as a catalyst, a metal precursor, which uses the fourth period transition metal, and a nitrogen-containing compound or a phosphorus-containing compound, and allowing the N,N-dialkylamide compound to react catalytically in the presence of an alcohol, and the present invention has been completed.

That is, the present invention relates to the following [1] to [9].

[1] A method for converting an N,N-dialkylamide compound into an ester compound, the method comprising using a fourth period transition metal complex as a catalyst, which is obtained by a reaction of a precursor having a fourth period transition metal with a nitrogen-containing compound or a phosphorus-containing compound.

[2] The method according to [1],
wherein the precursor is a metal complex having a ligand selected from the group consisting of beta-diketonates, beta-diketoiminates, and beta-diketiminates, or a carboxylate of the fourth period transition metal,
the nitrogen-containing compound is a nitrogen-containing compound having two nitrogen atoms, and
the phosphorus-containing compound is a phosphorus-containing compound having two phosphorus atoms.

[3] The method according to [1] or [2], wherein the nitrogen-containing compound is bipyridine which may have substituent(s) or 1,10-phenanthroline which may have substituent(s).

[4] A fourth period transition metal complex, which is obtained by a reaction of a precursor having a fourth period transition metal with a nitrogen-containing compound or a phosphorus-containing compound in the presence of an alcohol or alkoxide.

[5] The fourth period transition metal complex according to [4],
wherein the precursor is a metal complex having a ligand selected from the group consisting of beta-diketonates, beta-diketoiminates, and beta-diketiminates, or a carboxylate of the fourth period transition metal,
the nitrogen-containing compound is a nitrogen-containing compound having two nitrogen atoms, and
the phosphorus-containing compound is a phosphorus-containing compound having two phosphorus atoms.

[6] The fourth period transition metal complex according to [4] or [5], wherein the nitrogen-containing compound is bipyridine which may have substituent(s) or 1,10-phenanthroline which may have substituent(s).

[7] A μ-oxo-dimer complex represented by the following general formula (1),

[Chem. 1]

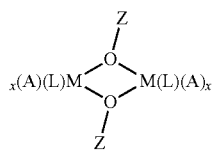

(1)

wherein M represents a fourth period transition metal,
A represents a carboxylic acid residue, a beta-diketonate, a beta-diketoiminate, or a beta-diketiminate,
in the case where A represents the carboxylic acid residue, x represents 2, and in the case where A represents the beta-diketonate, beta-diketoiminate, or beta-diketiminate, x represents 1,
L represents a nitrogen-containing compound or a phosphorus-containing compound, and
Z represents a lower alkyl group which may have substituent(s), a lower alkoxy group which may have substituent(s), a lower alkenyl group which may have substituent(s), a lower alkynyl group which may have substituent(s), a halo-lower alkyl group which may have substituent(s), a halo-lower alkenyl group which may have substituent(s), a halo-lower alkynyl group which may have substituent(s), a cyclic hydrocarbon group which may have substituent(s), or a heterocyclic group which may have substituent(s),
the μ-oxo-dimer complex being obtained by a reaction of a metal complex having a ligand selected from the group consisting of beta-diketonates, beta-diketoiminates, and beta-diketiminates, or a carboxylate of a fourth period transition metal, with a nitrogen-containing compound or phosphorus-containing compound, which are added thereto, in the presence of an alcohol or alkoxide.

[8] A method for producing an amidated compound, comprising allowing an amine to react with a carboxylic acid ester in the presence of the fourth period transition metal complex according to any one of [4] to [6].

[9] A method of causing a transesterification reaction in the presence of the fourth period transition metal complex according to any one of [4] to [6].

Advantageous Effects of Invention

The present invention provides an efficient catalytic reaction of converting an N,N-dialkylamide, which is a tertiary amide, into an ester compound, and a fourth period transition metal complex used as a catalyst in the reaction.

By using the catalytic reaction in the present invention, a tertiary amide compound with a large steric hindrance that does not facilitate transesterification reaction can also be converted into an ester compound. As a result, environmental compatibility, operability, and economic efficiency are expected to be improved as compared with the related art.

By using the fourth period transition metal complex in the present invention, the amide bonds, which have been difficult to be used flexibly in synthetic chemistry due to the high stability thereof in the related art, can be used as a protecting group of a carbonyl group or an orientation group, and it can be applied to production of pharmaceutical intermediates or agrochemical intermediates, functional materials, structural materials, or the like.

DESCRIPTION OF EMBODIMENTS

Figure 1:
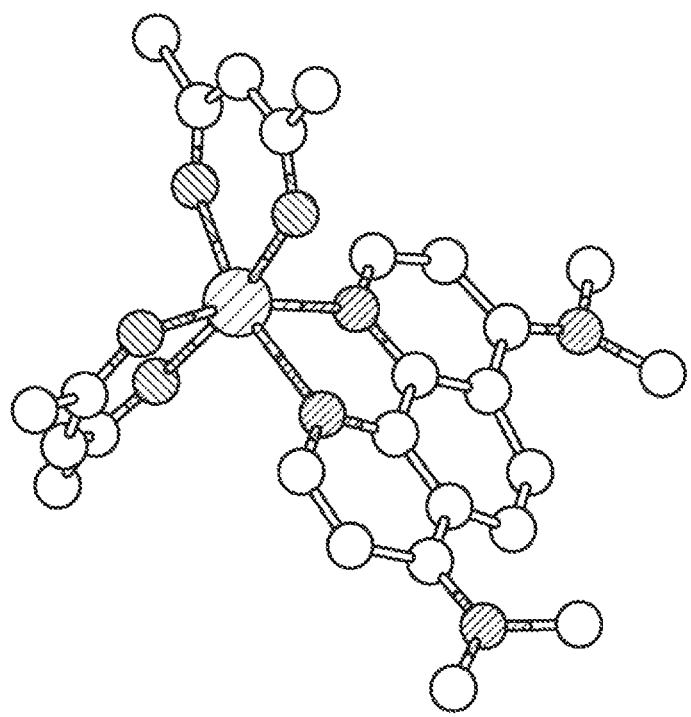
FIG. 1 shows results of X-ray crystal structure analysis of a manganese complex obtained in Example 79, which has 1,10-phenanthroline having a dimethylamino group at the 4- and 7-positions.

Hereinafter, the present invention is described specifically, but the present invention is not limited to the following embodiments, and can be carried out in any manner without departing from the scope of the present invention.

In the present description, Me means a methyl group, Et means an ethyl group, Bu means a butyl group, Pr means a propyl group, Ph and Phenyl means a phenyl group, Tol and Tolyl mean a tolyl group, and phen means phenanthroline.

In the method for converting an N,N-dialkylamide compound into an ester compound in the present invention, a fourth period transition metal complex, which is obtained by a reaction of a precursor having a fourth period transition metal with a nitrogen-containing compound or phosphorus-containing compound, is used as a catalyst <Fourth Period Transition Metal Complex>

The fourth period transition metal complex can be obtained from a precursor having a fourth period transition metal described below, and a nitrogen-containing compound or a phosphorus-containing compound (also referred to as a ligand (L) below). Namely, the fourth period transition metal complex can be obtained by adding a nitrogen-containing heterocyclic compound or a phosphorus-containing compound to the precursor having a fourth period transition metal in the presence of a suitable solvent.

A detailed method for producing the fourth period transition metal complex is described below.

Examples of the fourth period transition metal include scandium (Sc), titanium (Ti), vanadium (V), chromium (Cr), manganese (Mn), iron (Fe), cobalt (Co), nickel (Ni), and copper (Cu). The fourth period transition metal is a metal having a vacant orbital in a 3d orbital of an inner shell. The fourth period transition metal is preferably manganese, iron, cobalt, nickel, or copper, is more preferably manganese or cobalt, and is further preferably manganese.

<Precursor Having Fourth Period Transition Metal>

The precursor having the fourth period transition metal in the present invention (also referred to as "metal precursor") may be an inorganic salt or an organometallic complex, or may be an anhydride or a hydrate.

Examples of the inorganic salt include halides, hydroxides, sulfides, phosphates, sulfates, nitrates, perchlorates, and the like, and the inorganic salt is preferably halides. Examples of the organometallic complex include metal alkoxides, metal aryl oxides, metal triflates, metal tosylates, metal mesylates, metal carboxylates (carboxylates), or hydrates thereof.

The organometallic complex may be any one having a ligand capable of coordinating with a metal, and preferably has a bidentate ligand. Preferable examples of the organometallic complex include metal complexes having a beta (β)-diketonate, beta (β)-diketoiminate, or beta (β)-diketiminate as a ligand.

Among them, from the viewpoint of efficient conversion to an ester compound, the organometallic complex is preferred, and the metal complex having a ligand selected from the group consisting of beta-diketonates, beta-diketoiminates, and beta-diketiminates, or the carboxylic acid metal salt (carboxylate) is more preferred.

The beta-diketonates are represented by the following general formula (2), the beta-diketoiminates are represented by the following general formula (3), and the beta-diketiminates are represented by the following general formula (4).

[Chem. 2]

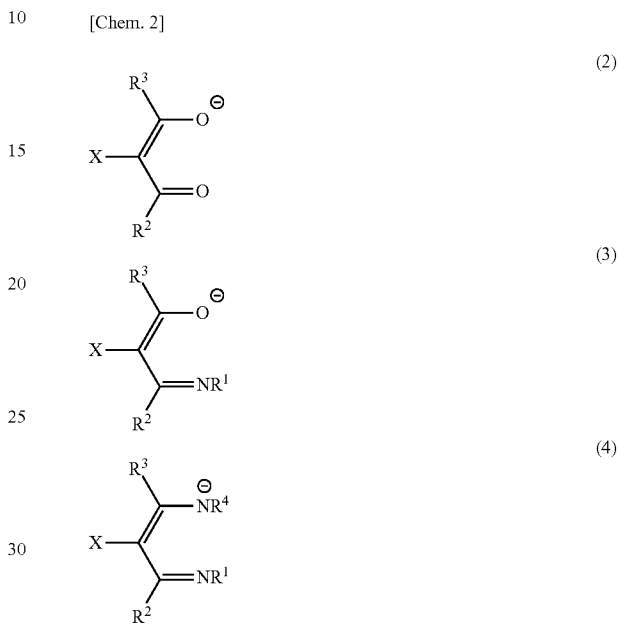

In the formulas (2) to (4), $R^1$, $R^2$, $R^3$ and $R^4$ each independently represent a hydrogen atom, a saturated hydrocarbon group having 1 to 20 carbon atoms, which may have substituent(s), an aryl group which may have substituent(s), a heteroaryl group which may have substituent(s), and a perfluoroalkyl group having 1 to 20 carbon atoms, which may have substituent(s), and the saturated hydrocarbon group having 1 to 20 carbon atoms, which may have substituent(s), is preferred. $R^1$, $R^2$, $R^3$ and $R^4$ more preferably represent a straight-chain or branched alkyl group having 1 to 5 carbon atoms, such as a methyl group, an ethyl group, an n-propyl group, an isopropyl group, an n-butyl group, an isobutyl group, a tert-butyl group, and a pentyl group.

X each independently represent a hydrogen atom, a saturated hydrocarbon group having 1 to 20 carbon atoms, which may have substituent(s), an aryl group which may have substituent(s), a heteroaryl group which may have substituent(s), and a perfluoroalkyl group having 1 to 20 carbon atoms, which may have substituent(s), and the saturated hydrocarbon group having 1 to 20 carbon atoms, which may have substituent(s), is preferred. X more preferably represents a hydrogen atom, or a straight-chain or branched alkyl group having 1 to 5 carbon atoms, such as a methyl group, an ethyl group, an n-propyl group, an isopropyl group, an n-butyl group, an isobutyl group, a tert-butyl group, and a pentyl group. X further preferably represents a hydrogen atom.

The organometallic complex is particularly preferably a manganese compound.

Examples of the manganese compound include manganese halide, manganese hydroxide, manganese alkoxides, manganese aryl oxide, manganese triflate, manganese tosylate, manganese mesylate, manganese acetylacetonate, manganese 2,2,6,6-tetramethylheptane-3,6-dionate (dipivaloyl methanate) (dpm), manganese carboxylate, or hydrates thereof. A divalent or trivalent manganese compound is preferred.

Examples of the divalent manganese compound include manganese (II) acetate ($Mn(CH_3CO_2)_2$), manganese (II) acetate tetrahydrate ($Mn(OAc)_2 \cdot 4H_2O$), manganese (II) formate ($Mn(HCOO)_2$), manganese (II) oxalate ($MnC_2O_4$), manganese (II) tartrate ($MnC_4H_4O_6$), manganese (II) oleate ($Mn(C_{17}H_{33}COO)_2$), manganese (II) chloride ($MnCl_2$), manganese (II) bromide ($MnBr_2$), manganese (II) fluoride ($MnF_2$), manganese iodide ($MnI_2$), manganese (II) hydroxide ($Mn(OH)_2$), manganese (II) sulfide (MnS), manganese (II) carbonate ($MnCO_3$), manganese (II) perchlorate ($Mn(ClO_4)_2$), manganese (II) sulfate ($MnSO_4$), manganese (II) nitrate ($Mn(NO_3)_2$), manganese (II) phosphates ($Mn_3(PO_4)_2$, $MnHPO_4$, and $Mn(H_2PO_4)_2$), manganese (II) diphosphate ($Mn_2P_2O_7$), manganese (II) hypophosphite ($H_4MnO_4P_2$), manganese (II) metaphosphate ($Mn(PO_3)_2$), manganese (II) arsenate ($Mn_3(AsO_4)_2$), manganese (II) borate ($MnB_4O_7$), manganese (II) acetylacetonate ($Mn(acac)_2$), manganese (II) acetylacetonate dihydrate ($Mn(acac)_2 \cdot 2H_2O$), bis(dipivaloylmethanate)manganese (II) ($Mn(dpm)_2$), bis(hexafluoroacetylacetonate)manganese (II) ($Mn(hfac)_2$), bis(hexafluoroacetylacetonate)manganese (II) dihydrate ($Mn(hfac)_2 \cdot 2H_2O$), and the like.

Examples of the trivalent manganese compound include manganese (III) acetate ($Mn(CH_3CO_2)_3$), manganese (III) acetate dihydrate ($Mn(OAC)_3 \cdot 2H_2O$), manganese (III) formate ($Mn(HCOO)_3$), manganese (III) fluoride ($MnF_3$), manganese (III) hydroxide (MnO(OH)), manganese (III) sulfate ($Mn_2(SO_4)_3$), manganese (III) phosphate ($MnPO_4$), manganese (III) diphosphate ($Mn_4(P_2O_7)_3$), manganese (III) arsenate ($MnAsO_4$), manganese (III) acetylacetonate ($Mn(acac)_3$), tris(dipivaloylmethanate)manganese (III) ($Mn(dpm)_3$), and the like.

The manganese compound is preferably an organic manganese complex, and more preferably manganese carboxylates (manganese acetate, etc.), or a manganese complex having a ligand selected from the group consisting of beta-diketonates, beta-diketoiminates, and beta-diketiminates.

Examples of the beta-diketonates include dipivaloyl methanate(2,2,6,6-tetramethyl-3,5-heptanedionate), 2,6-dimethyl-3,5-heptandionate, 2,2,6,6-tetramethyl-3,5-octanedionate, 2,2,6-trimethyl-3,5-heptandionate, 6-ethyl-2,2-dimethyl-3,5-octanedionate, and the like. The beta-diketonates are further preferably manganese acetylacetonate and manganese dipivaloylmethanate.

<Nitrogen-Containing Compound>

In the present invention, examples of the nitrogen-containing compound include aliphatic amines, aromatic amines, and nitrogen-containing heterocyclic compounds. These nitrogen-containing compounds may have substituent(s).

The aliphatic amines mean a compound obtained by substituting a hydrogen atom of ammonia ($NH_3$) with aliphatic groups. Examples of the aliphatic groups include straight-chain or branched alkyl groups having 1 to 10 carbon atoms, or alicyclic groups, and the aliphatic groups are more preferably straight-chain or branched alkyl groups having 1 to 6 carbon atoms, or alicyclic groups. The aliphatic amines may have substituent(s).

Specific examples of the aliphatic amines include ethylenediamine, methylamine, ethylamine, propylamine, butylamine, isopropylamine, 2-ethylhexylamine, tert-butylamine, diethylamine, diisopropylamine, triethylamine, tributylamine, diethylenetriamine, triethylenetetramine, tris(2,2',2''-aminoethyl)amine, N,N'-bis(2-aminoethyl)-1,3-propanediamine, N,N'-bis(3-aminopropyl)ethylenediamine, bis(3-aminopropyl)amine, 1,2-bis(3-aminopropylamino)ethane, 1,4-bis(3-aminopropyl)piperidine, cyclopropylamine, cyclohexylamine, and the like.

The aliphatic amines are preferably ethylenediamine, diethylenetriamine, triethylenetetramine, tris(2,2',2''-aminoethyl)amine, N,N'-bis(2-aminoethyl)-1,3-propanediamine, N,N'-bis(3-aminopropyl)ethylenediamine, bis(3-aminopropyl)amine, 1,2-bis(3-aminopropylamino)ethane, 1,4-bis(3-aminopropyl)piperidine, or the like, and more preferably ethylenediamine having a substituent, or diethylenetriamine having a substituent.

The aromatic amines mean a compound obtained by substituting a hydrogen atom of ammonia with aromatic groups. Examples of the aromatic groups include aromatic groups including a single ring or a plurality of rings (fused rings).

Specific examples of the aromatic amines include aniline, toluidine, xylidine, anisidine, naphthylamine, diphenylamine, triphenylamine, benzidine, 1,2-phenylenediamine, 4-fluoro-1,2-phenylenediamine, 2,3-diaminotoluene, 3,4-diaminotoluene, 3,3'-diaminobenzidine, 3,4-diaminobenzophenone, 4,5-dichloro-1,2-phenylenediamine, 3,4-diaminobenzoic acid, and the like.

The aromatic amines are preferably 1,2-phenylenediamine, 4-fluoro-1,2-phenylenediamine, 2,3-diaminotoluene, 3,4-diaminotoluene, 3,3'-diaminobenzidine, 3,4-diaminobenzophenone, 4,5-dichloro-1,2-phenylenediamine, 3,4-diaminobenzoic acid, and the like.

The aromatic amines may have substituent(s). The aromatic amines may preferably have straight-chain or branched alkyl groups having 1 to 10 carbon atoms, or alicyclic groups, as a substituent.

Examples of the nitrogen-containing heterocyclic compound include compounds including a single ring or a plurality of rings (fused rings) having a heterocycle, and the nitrogen-containing heterocyclic compound may have substituent(s).

Specific examples of substituted or unsubstituted nitrogen-containing heteromonocyclic compounds include pyridine, bipyridines such as 2,2'-bipyridine, 2,3-diaminopyridine, 3,4-diaminopyridine, 2,5-diamino-5-bromopyridine, 6,6'-diamino-2,2'-bipyridyl, 2,2'-bi-4-picoline, 6,6'-bi-3-picoline, phthalocyanine, 2,2'-biquinoline, and 4-dimethylaminopyridine (DMAP).

The substituted or unsubstituted nitrogen-containing heteromonocyclic compounds are preferably pyridine having a substituent, further preferably 4-dimethylaminopyridine (DMAP), unsubstituted bipyridine or bipyridine which may have substituent(s), and particularly preferably bipyridine having an electron donating group as a substituent.

Examples of the electron donating group include alkyl groups having 1 to 50 carbon atoms, alkoxy groups, and substituted amino groups. The electron donating group is further preferably substituted amino groups.

Examples of substituted or unsubstituted nitrogen-containing heterocyclic fused ring compounds include 1-indoline, 2-indoline, 3-indoline, 4-indoline, 5-indoline, 6-indoline, 7-indoline, 1-isoindoline, 2-isoindoline, 3-isoindoline, 4-isoindoline, 5-isoindoline, 6-isoindoline, 7-isoindoline, quinoline, 3-quinoline, 4-quinoline, 5-quinoline, 6-quinoline, 7-quinoline, 8-quinoline, 1-isoquinoline, 3-isoquinoline, 4-isoquinoline, 5-isoquinoline, 6-isoquinoline, 7-isoquinoline, 8-isoquinoline, 2-quinoxaline, 5-quinoxaline, 6-quinoxaline, 1-carbazoline, 2-carbazoline, 3-carbazoline, 4-carbazoline, 9-carbazoline, 1-phenanthridine, 2-phenanthridine, 3-phenanthridine, 4-phenanthridine, 6-phenanthridine, 7-phenanthridine, 8-phenanthridine, 9-phenanthridine, 10-phenanthridine, 1-acridine, 2-acridine, 3-acridine, 4-acridine, 9-acridine, 1,7-phenanthroline, 1,8-phenanthroline, 1,9-phenanthroline, 1,10-phenanthroline, 2,9-phenanthroline, 2,8-phenanthroline, 2,7-phenanthroline, 1-phenazine, 2-phenazine, 1-phenothiazine, 2-phenothiazine, 3-phenothiazine, 4-phenothiazine, 10-phenothiazine, 1-phenoxazine, 2-phenoxazine, 3-phenoxazine, 4-phenoxazine, 10-phenoxazine, 2-methyl-1-indoline, 4-methyl-1-indoline, 2-methyl-3-indoline, 4-methyl-3-indoline, 2-tert-butyl-1-indoline, 4-tert-butyl-1-indoline, 2-tert-butyl-3-indorine, 4-tert-butyl-3-indoline, and the like.

The nitrogen-containing compound may be any one as long as it is a ligand capable of coordinating with the fourth period transition metal, and is preferably a bidentate ligand. The nitrogen-containing compound is preferably a nitrogen-containing compound having two nitrogen atoms. Among the nitrogen-containing compounds having two nitrogen atoms, more preferable examples thereof include bipyridine and phenanthroline. Unsubstituted 2,2'-bipyridine or 2,2'-bipyridine having a substituent, or 1,10-phenanthroline is further preferred. 1,10-phenanthroline having a substituent is further preferred, and 1,10-phenanthroline having an electron donating group as a substituent is particularly preferred.

Examples of the substituent that may be contained in the nitrogen-containing compound include a halogen atom (such as a fluorine atom, a chlorine atom, a bromine atom and an iodine atom), an alkyl group, a non-fused ring aryl group, a non-fused ring heteroaryl group, a substituted amino group, and an alkoxy group.

Preferable examples of the substituent that may be contained in the nitrogen-containing compound include electron donating groups. Examples of the electron donating group include alkyl groups having 1 to 50 carbon atoms, alkoxy groups, and substituted amino groups. The electron donating group is further preferably substituted amino groups.

Examples of the non-fused ring aryl group include non-fused ring aryl groups having 6 to 20 ring-forming carbon atoms, and examples of the non-fused ring heteroaryl group include non-fused ring heteroaryl groups having 5 to 20 ring-forming atoms.

The alkyl group having 1 to 50 carbon atoms may be straight-chain or branched, and may be a cycloalkyl group. Specific examples of the alkyl group include chain alkyl groups such as a methyl group, an ethyl group, an n-propyl group, an isopropyl group, an n-butyl group, an isobutyl group, a sec-butyl group, a tert-butyl group, an n-pentyl group, an isopentyl group, a 2-methylbutyl group, a 1-methylbutyl group, an n-hexyl group, an isohexyl group, a 3-methylpentyl group, a 2-methylpentyl group, a 1-methylpentyl group, a heptyl group, an octyl group, an isooctyl group, a 2-ethylhexyl group, a 3,7-dimethyloctyl group, a nonyl group, a decyl group, an undecyl group, a dodecyl group, a tetradecyl group, a hexadecyl group, an octadecyl group, and an eicosyl group, and cycloalkyl groups such as a cyclopentyl group, a cyclohexyl group, and an adamantyl group.

The alkoxy group may be straight-chain or branched, and may be a cycloalkoxy group.

The alkoxy group may have substituent(s). The number of carbon atoms of the alkoxy group is generally about 1 to 20, and specific examples of the alkoxy group include a methoxy group, an ethoxy group, a propoxy group, an isopropoxy group, a butoxy group, an isobutoxy group, a tert-butoxy group, a pentoxy group, a hexyloxy group, a cyclohexyloxy group, a heptyloxy group, an octyloxy group, a 2-ethylhexyloxy group, a nonyloxy group, a decyloxy group, a 37-dimethyloctyloxy group, a lauryloxy group, a trifluoromethoxy group, a pentafluoroethoxy group, a perfluorobutoxy group, a perfluorohexyl group, a perfluorooctyl group, a methoxymethyloxy group, and a 2-methoxyethyloxy group.

Preferable examples of the alkoxy group include a methoxy group, an ethoxy group, a propoxy group, an isopropoxy group, a butoxy group, an isobutoxy group, and a tert-butoxy group.

The number of carbon atoms of the substituted amino group is generally about 1 to 40. Specific examples of the substituted amino group include a methylamino group, a dimethylamino group, an ethylamino group, a diethylamino group, a propylamino group, a dipropylamino group, an isopropylamino group, a diisopropylamino group, a butylamino group, an isobutylamino group, a tert-butylamino group, a pentylamino group, a hexylamino group, a cyclohexylamino group, a heptylamino group, an octylamino group, a 2-ethylhexylamino group, a nonylamino group, a decylamino group, a 3,7-dimethyloctylamino group, a laurylamino group, a cyclopentylamino group, a dicyclopentylamino group, a cyclohexylamino group, a dicyclohexylamino group, a pyrrolidyl group, a piperidyl group, a ditrifluoromethylamino group, a phenylamino group, a diphenylamino group, a $C_{1-12}$ alkoxy phenyl amino group, a di($C_{1-12}$ alkoxy phenyl) amino group, a di($C_{1-12}$ alkylphenyl) amino group, a 1-naphthylamino group, a 2-naphthylamino group, a pentafluorophenylamino group, a pyridylamino group, a pyridazinylamino group, a pyrimidylamino group, a pyrazylamino group, a triazylamino group, a phenyl-$C_{1-12}$ alkylamino group, a $C_{1-12}$ alkoxyphenyl-$C_{1-12}$ alkylamino group, a $C_{1-12}$ alkylphenyl-$C_{1-12}$ alkylamino group, a di($C_{1-12}$ alkoxyphenyl-$C_{1-12}$ alkyl) amino group, a di($C_{1-12}$ alkylphenyl-$C_{1-12}$ alkyl) amino group, a 1-naphthyl-$C_{1-12}$ alkylamino group, and a 2-naphthyl-$C_{1-12}$ alkylamino group.

The substituted amino group is preferably a methylamino group, a dimethylamino group, an ethylamino group, a diethylamino group, a propylamino group, a dipropylamino group, an isopropylamino group, a diisopropylamino group, a butylamino group, an isobutylamino group, or a tert-butylamino group. The substituted amino group is further preferably a dimethylamino group, a diethylamino group, a dipropylamino group, or a diisopropylamino group.

<Phosphorus-Containing Compound>

Instead of the nitrogen-containing compound, a phosphorus-containing compound may be used as a ligand of a metal.

The phosphorus-containing compound may be a monodentate ligand or a bidentate ligand.

The phosphorus-containing compound may have substituent(s). Examples of the substituent that may be contained in the phosphorus-containing compound include an alkyl group, a non-fused ring aryl group, a non-fused ring heteroaryl group, a substituted amino group, and an alkoxy group, and specific examples thereof are as described above.

Examples of the monodentate ligand include phosphine compounds and phosphite compounds.

Examples of the bidentate ligand include diphosphine compounds and aminophosphine compounds.

Specific examples of the phosphorus-containing compound include phosphane compounds such as triphenylphosphine, tritolylphosphine, trimethylphosphine, triethylphosphine, methyldiphenylphosphine, dimethylphenylphosphine, bis(diphenylphosphino)methane (dppm), bis(diphenylphosphino)ethane (dppe), bis(diphenylphosphino)propane (dppp), bis(diphenylphosphino)butane (dppb), and bis(diphenylphosphino)ferrocene (dppf), and phosphite compounds such as trimethyl phosphite, triethyl phosphite, and triphenyl phosphite.

Examples of bidentate phosphorus-containing compounds include phosphorus-containing compounds represented by the following general formula (B).

$R^{P1}R^{P2}P\text{-}Q\text{-}PR^{P3}R^{P4}$ (B)

(In the formula (B), $R^{P1}$, $R^{P2}$, $R^{P3}$, and $R^{P4}$ each independently represent an aryl group which may have substituent(s), a cycloalkyl group which may have substituent(s), or an alkyl group which may have substituent(s), and $R^{P1}$ and $R^{P2}$ and/or $R^{P3}$ and $R^{P4}$ may form rings. Q represents a divalent arylene group which may have substituent(s) or a ferrocenediyl group which may have substituent(s).)

In the above formula, examples of the aryl group which is represented by $R^{P1}$, $R^{P2}$, $R^{P3}$, and $R^{P4}$ and may have substituent(s) include aryl groups having 6 to 14 carbon atoms, and specific examples thereof include a phenyl group, a naphthyl group, an anthryl group, a phenanthryl group, a biphenyl group, and the like. These aryl groups may have one or two or more substituents, and examples of the substituent include an alkyl group, an alkoxy group, an aryl group, a heterocyclic group, and the like.

Examples of the alkyl group as the substituent for the aryl group include straight-chain or branched alkyl groups having 1 to 15 carbon atoms, preferably 1 to 10 carbon atoms, and more preferably 1 to 6 carbon atoms, and specific examples thereof include a methyl group, an ethyl group, an n-propyl group, an isopropyl group, an n-butyl group, an s-butyl group, an isobutyl group, a tert-butyl group, and the like.

Examples of the alkoxy group as the substituent for the aryl group include straight-chain or branched alkoxy groups having 1 to 6 carbon atoms, and specific examples thereof include a methoxy group, an ethoxy group, an n-propoxy group, an isopropoxy group, an n-butoxy group, an s-butoxy group, an isobutoxy group, a tert-butoxy group, and the like.

Examples of the aryl group as the substituent for the aryl group include aryl groups having 6 to 14 carbon atoms, and specific examples thereof include a phenyl group, a naphthyl group, an anthryl group, a phenanthryl group, a biphenyl group, and the like.

Examples of the heterocyclic group as the substituent for the aryl group include an aliphatic heterocyclic group and an aromatic heterocyclic group.

Examples of the aliphatic heterocyclic group include an aliphatic heterocyclic group which has a single ring with 5- to 8-membered ring, preferably 5- or 6-membered ring, which contains 2 to 14 carbon atoms and contains at least 1, preferably 1 to 3, hetero atoms, such as a nitrogen atom, an oxygen atom, and a sulfur atom, or a polycycle or fused ring including these single rings.

Specific examples of the aliphatic heterocyclic group include a 2-oxopyrrolidyl group, a piperidino group, a piperazinyl group, a morpholino group, a tetrahydrofuryl group, a tetrahydropyranyl group, a tetrahydrothienyl group, and the like.

On the other hand, examples of the aromatic heterocyclic group include a heteroaryl group which has a single ring with 5- to 8-membered ring, preferably 5- or 6-membered ring, which contains 2 to 15 carbon atoms and contains at least 1, preferably 1 to 3, hetero atoms, such as a nitrogen atom, an oxygen atom, and a sulfur atom, or a polycycle or fused ring including these single rings.

Specific examples thereof include a furyl group, a thienyl group, a pyridyl group, a pyrimidinyl group, a pyrazinyl group, a pyridazinyl group, a pyrazolyl group, an imidazolyl group, an oxazolyl group, a thiazolyl group, a benzofuryl group, a benzothienyl group, a quinolyl group, an isoquinolyl group, a quinoxalyl group, a phthalazinyl group, a quinazolinyl group, a naphthyridinyl group, a cinnolinyl group, a benzimidazolyl group, a benzoxazolyl group, a benzothiazolyl group, and the like.

Examples of the cycloalkyl group which is represented by $R^{P1}$, $R^{P2}$, $R^{P3}$, and $R^{P4}$ and may have substituent(s) include a cycloalkyl group having a 5- or 6-membered ring, and preferable examples of the cycloalkyl group include a cyclopentyl group, a cyclohexyl group, and the like. One or two or more groups on the ring of these cycloalkyl groups may be substituted with a substituent, such as the alkyl group or alkoxy group, which is exemplified as a substituent for the aryl group.

Examples of an alkyl group which is represented by $R^{P1}$, $R^{P2}$, $R^{P3}$, and $R^{P4}$ and may have substituent(s) include straight-chain or branched alkyl groups having 1 to 15 carbon atoms, preferably 1 to 10 carbon atoms, and more preferably 1 to 6 carbon atoms. Specific examples thereof include a methyl group, an ethyl group, an n-propyl group, an isopropyl group, an n-butyl group, an s-butyl group, an isobutyl group, a tert-butyl group, a pentyl group, a hexyl group, and the like. These alkyl groups may have one or two or more substituents, and examples of the substituents include an alkoxy group, halogen atoms, and the like. Examples of the alkoxy group include the alkoxy group described as the substituent for the aryl group.

Examples of the ring which may be formed by $R^{P1}$ and $R^{P2}$ and/or $R^{P3}$ and $R^{P4}$ include a ring such as a four-membered ring, a five-membered ring, and a six-membered ring as a ring containing a phosphorus atom to which $R^{P1}$, $R^{P2}$, $R^{P3}$, and $R^{P4}$ are bonded. Examples of the specific rings include a phosphetane ring, a phospholane ring, a phosphane ring, a 2,4-dimethylphosphetane ring, a 2,4-diethylphosphetane ring, a 2,5-dimethylphosphorane ring, a 2,5-dimethylphosphorane ring, a 2,6-dimethylphosphane ring, a 2,6-diethylphosphane ring, and the like, and these rings may be optically active substances.

Examples of the divalent arylene group which is represented by Q and may have substituent(s) include arylene groups having 6 to 20 carbon atoms, such as a phenylene group, a biphenyldiyl group, and a binaphthalene diyl group.

Examples of the phenylene group include a o-phenylene group and a m-phenylene group, and the phenylene group may have a group substituted with the following groups including: alkyl groups having 1 to 4 carbon atoms, such as a methyl group, an ethyl group, an n-propyl group, an isopropyl group, an n-butyl group, an s-butyl group, an isobutyl group, and a tert-butyl group, alkoxy groups having 1 to 4 carbon atoms, such as a methoxy group, an ethoxy group, an n-propoxy group, an isopropoxy group, an n-butoxy group, an s-butoxy group, an isobutoxy group, and a tert-butoxy group; and a hydroxyl group, an amino group, or a substituted amino group (substituents for the substituted amino group being alkyl groups having 1 to 4 carbon atoms).

As the biphenyldiyl group and the binaphthalene diyl group, those having a structure of a 1,1'-biaryl-2,2'-diyl type are preferred, and the biphenyldiyl group and the binaphthalene diyl group may have a group substituted with the alkyl groups, alkoxy groups, alkylenedioxy groups such as a methylenedioxy group, an ethylenedioxy group and a trimethylenedioxy group, a hydroxyl group, an amino group, or a substituted amino group, which are as described above.

The ferrocenediyl group may also have a substituent, and examples of the substituent include alkyl groups, alkoxy groups, alkylenedioxy groups, a hydroxyl group, an amino group, a substituted amino group, and the like.

The bidentate phosphorus-containing compound may have an optically active moiety, which may become an optically active compound, in a molecule thereof. Examples of the bidentate phosphorus-containing compound having an optically active moiety include an optically active bidentate phosphine ligand represented by the following general formula (5).

[Chem. 3]

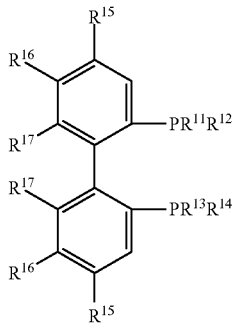

(5)

(In the formula (5), $R^{11}$ to $R^{14}$ each independently represent an aryl group which may have substituent(s), or a cycloalkyl group having 3 to 10 carbon atoms, and each of $R^{11}$ and $R^{12}$, and $R^{13}$ and $R^{14}$ may form a heterocycle together with a phosphorus atom adjacent thereto; $R^{15}$ and $R^{16}$ each independently represent a hydrogen atom, alkyl groups having 1 to 5 carbon atoms, alkoxy groups having 1 to 5 carbon atoms, di($C_{1-5}$ alkyl) amino groups, 5-membered to 8-membered cyclic amino groups, or halogen atoms; $R^{17}$ represents alkyl groups having 1 to 5 carbon atoms, alkoxy groups having 1 to 5 carbon atoms, di($C_{1-5}$ alkyl) amino groups, 5-membered to 8-membered cyclic amino groups, or halogen atoms; each of $R^{15}$ and $R^{16}$, and $R^{16}$ and $R^{17}$ may form a fused benzene ring, a fused substituted benzene ring, a trimethylene group, a tetramethylene group, a pentamethylene group, a methylenedioxy group, an ethylenedioxy group, or a trimethylenedioxy group.)

Specific examples of the phosphorus-containing compound include diphosphine compounds such as 1,2-bis(anisylphenylphosphino)ethane (DIPAMP), 1,2-bis(alkylmethylphosphino)ethane (BisP*), 2,3-bis(diphenylphosphino)butane (CHIRAPHOS), 1,2-bis(diphenylphosphino)propane (PROPHOS), 2,3-bis(diphenylphosphino)-5-norbornene (NORPHOS), 2,3-o-isopropylidene-2,3-dihydroxy-1,4-bis(diphenylphosphino)butane (DIOP), 1-cyclohexyl-1,2-bis(diphenylphosphino)ethane (CYCPHOS), 1-substituted-3,4-bis (diphenylphosphino)pyrrolidine (DEGPHOS), 2,4-bis-(diphenylphosphino)pentane (SKEWPHOS), 1,2-bis (substituted phosphorano)benzene (DuPHOS), 1,2-bis (substituted phosphorano)ethane (BPE), 1-{(substituted phosphorano)-2-(diphenylphosphino)benzene} (UCAP-Ph), 1-{bis(3,5-dimethylphenyl)phosphino}-2-(substituted phosphorano)benzene (UCAP-DM), 1-(substituted phosphorano)-2-[bis{3,5-di(tert-butyl)-4-methoxyphenyl}phosphino]benzene (UCAP-DTBM), 1-{(substituted phosphorano)-2-(di-naphthalen-1-yl-phosphino)benzene (UCAP-(1-Nap)}, 2,2'-bis(diphenylphosphino)-1,1'-bicyclopentane (BICP), 2,2'-bis(diphenylphosphino)-1,1'-binaphthyl (BINAP), 2,2'-bis(diphenylphosphino)-1,1'-(5,5',6,6',7,7',8,8'-octahydrobinaphthyl) ($H_8$-BINAP), 2,2'-bis(di-p-tolylphosphino)-1,1'-binaphthyl (TOL-BINAP), 2,2'-bis{di(3,5-dimethylphenyl)phosphino}-1,1'-binaphthyl (DM-BINAP), 2,2'-bis(diphenylphosphino)-6,6'-dimethyl-1,1'-biphenyl (BICHEP), (4,4'-bi-1,3-benzodioxole)-5,5'-diylbis (diphenylphosphine) (SEGPHOS), (4,4'-bi-1,3-benzodioxole)-5,5'-diylbis[bis(3,5-dimethylphenyl) phosphine] (DM-SEGPHOS), and [(4S)-(4,4'-bi-1,3-benzodioxole)-5,5'-diyl]bis[bis{3,5-bis(1,1-dimethylethyl)-4-methoxyphenyl}phosphine] (DTBM-SEGPHOS).

Among these compounds, the phosphorus-containing compound is preferably a phosphorus-containing compound having two phosphorus atoms, such as a diphosphine compound having electron conditions and arrangements that are easy to form coordination with the fourth period transition metal, from the viewpoint of efficient conversion to ester compounds, and the phosphorus-containing compound having two phosphorus atoms may be appropriately selected from those shown by the specific examples of the above phosphorus-containing compound.

The nitrogen-containing compound and the phosphorus-containing compound may be a bidentate aminophosphine compound having one phosphorus atom and one nitrogen atom.

Examples of the bidentate aminophosphine compound include optically active aminophosphine compounds represented by the following general formula (C).

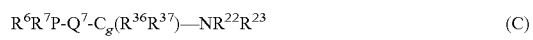

(C)

(In the formula (C), $Q^7$ represents a spacer or a valence bond, and may be any combination of an aryl group which may have substituent(s), a cycloalkyl group which may have substituent(s), and an alkyl group which may have substituent(s). $R^6$, $R^7$, $R^{22}$, and $R^{23}$ each independently represent an aryl group which may have substituent(s), a cycloalkyl group which may have substituent(s), or an alkyl group which may have substituent(s), and $R^{36}$ and $R^{37}$ each independently represent a hydrogen atom, a hydrocarbon group which may have substituent(s), or a heterocyclic group which may have substituent(s). g represents 0 or 1. $R^{22}$ or $R^{23}$, $R^{36}$ or $R^{37}$, $C_g$, and N may be bonded to each other to form a ring such as a carbocyclic ring or an aliphatic ring.)

In the formula (C), as the aryl group which may have substituent(s) and the cycloalkyl group which may have substituent(s), the same groups as those that may be used in the above general formula (B) may be used.

Examples of the hydrocarbon group which may have substituent(s) include an aryl group, a cycloalkyl group, an alkyl group, and the like. As the alkyl group, the same groups as those that may be used in the above general formula (B) may be used.

Examples of the heterocyclic group which may have substituent(s) include an aliphatic heterocyclic group, an aromatic heterocyclic group, and the like.

Examples of the aliphatic heterocyclic group include an aliphatic heterocyclic group which has a single ring with 5- to 8-membered ring, preferably 5- or 6-membered ring, which contains 2 to 14 carbon atoms and contains at least 1, preferably 1 to 3, hetero atoms, such as a nitrogen atom, an oxygen atom, and a sulfur atom, or a polycycle or fused ring including these single rings.

Examples of the aromatic heterocyclic group include a heteroaryl group which has a single ring with 5- to 8-membered ring, preferably 5- or 6-membered ring, which contains 2 to 15 carbon atoms and contains at least 1, preferably 1 to 3, hetero atoms, such as a nitrogen atom, an oxygen atom, and a sulfur atom, or a polycycle or fused ring including these single rings.

As the above substituent, the same substituent as the substituent which may be contained in the aryl group in the above general formula (B) may be used.

The bidentate aminophosphine compound may be the following compounds having an optically active moiety, which may become an optically active compound, in a molecule thereof.

[Chem. 4]

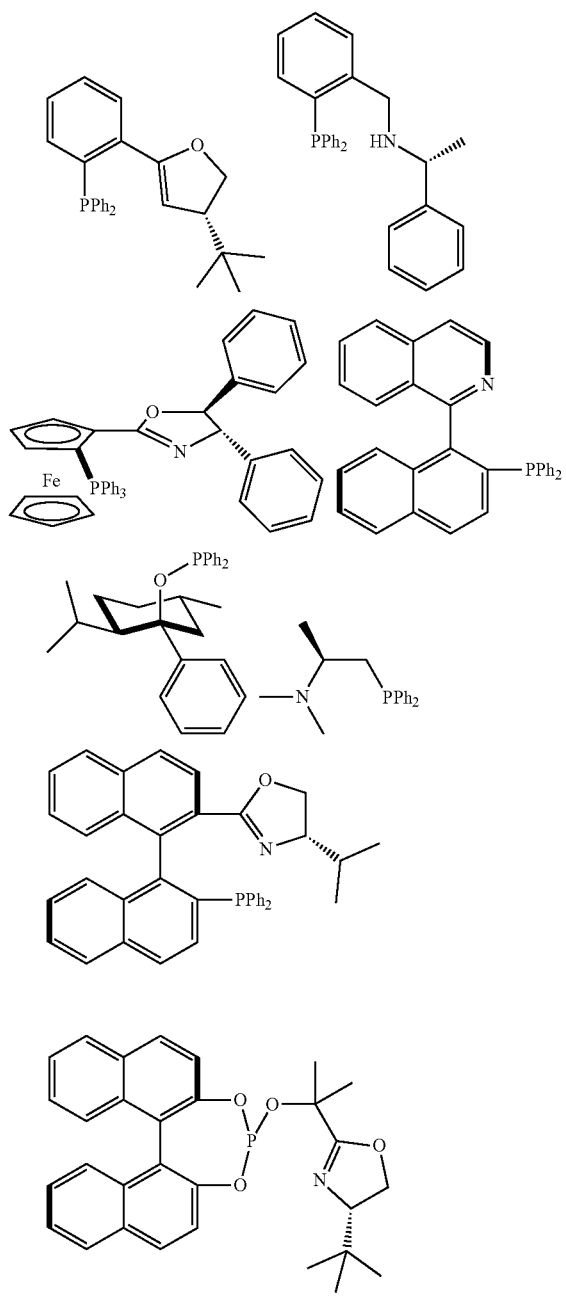

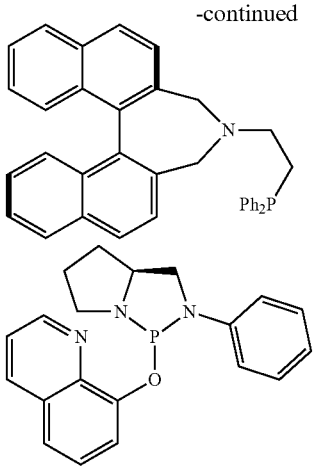

The bidentate aminophosphine compound may be the following aminophosphine compound.

[Chem. 5]

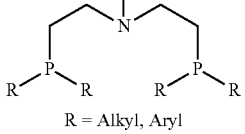

R = Alkyl, Aryl

<Method for Producing Fourth Period Transition Metal Complex>

The fourth period transition metal complex in the present invention can be produced, for example, by adding a nitrogen-containing compound or phosphorus-containing compound to a metal precursor.

in the case where the number of nitrogen atoms or phosphorus atoms in the nitrogen-containing compound or the phosphorus-containing compound is two, an addition amount of the nitrogen-containing compound or phosphorus-containing compound is not less than equimolar amount of the metal precursor, preferably not less than 1.1 times the molar amount of the metal precursor, and in the case where the number of nitrogen atoms or phosphorus atoms in the nitrogen-containing compound or the phosphorus-containing compound is one, the addition amount thereof is not less than 2 times, preferably not less than 2.2 times the molar amount of the metal precursor.

As a solvent used in the addition of the nitrogen-containing compound or the phosphorus-containing compound, any solvent can be used as long as it does not affect the formation of the fourth period transition metal complex in the present invention. In addition, a solvent, in which the metal precursor, and the nitrogen-containing compound or the phosphorus-containing compound, which are used as raw materials, can be dissolved, is preferred. For example, tetrahydrofuran (THF), benzene, toluene, xylene, hexane, heptane, octane, alcohols, and the like can be used. A solvent such as the alcohols or THF is preferred, and the alcohols are more preferred.

The reaction temperature is preferably equal to or higher than the temperature at which the metal precursor and the nitrogen-containing compound or the phosphorus-containing compound, which are used as raw materials, can be dissolved, and is from 30° C. to 250° C., more preferably from 80° C. to 160° C.

The reaction time is not particularly limited, and is generally about 1 hour to 45 hours, and preferably about 2 hours to 24 hours. These conditions can be appropriately changed depending on the kinds and amounts of used raw materials and the like.

The fourth period transition metal complex in the present invention obtained under the above conditions is stable in air, but is preferably handled in the presence of an inert gas. The inert gas is preferably nitrogen, argon, or the like.

In the case where the fourth period transition metal complex in the present invention is used as a catalyst, after the fourth period transition metal complex prepared in advance in the presence of an appropriate solvent (for example, alcohol) is obtained, it may be added to a reaction system. In this way, a catalyst formed of the fourth period transition metal complex in the present invention can be obtained by adding a nitrogen-containing compound or phosphorus-containing compound to a metal precursor and allowing them to react with each other.

By the reaction in the presence of an alcohol, a fourth period transition metal complex in which an oxygen atom derived from the alcohol is crosslinked with two metal atoms composed of a fourth period transition metal can be obtained. The fourth period transition metal complex in the present invention mainly works as a catalyst for an ester conversion from an amide compound.

Examples of the metal precursor include compounds composed of a fourth period transition metal M, a carboxylic acid residue, a beta (β)-diketonate, a beta (β)-diketoiminate, or a beta (β)-diketiminate, which is represented by A, such as compounds represented by the general formula (15) described below.

β-diketones tend to particularly form an enol or an enolate (beta (β)-diketonates), which is a tautomer of β-diketones. This is because the enol or enolate is conjugated with another carbonyl group, and in a case where a complex is formed (for example, with manganese), the enol or enolate contributes to the stability obtained by forming a 6-membered ring. The same applies to β-diketone imines and β-diketimines.

Examples of β-diketones include acetylacetone, 2,4-pentanedione, 1,3-bis(p-methoxyphenyl)-1,3-propanedione, 5,5-dimethyl-1,3-cyclohexanedione, 2,6-dimethyl-3,5-heptanedione, 1,3-di(2-naphthyl)-1,3-propanedione, 1,3-diphenyl-1,3-propanedione, 2,4-hexanedione, 6-methyl-2,4-pentanedione, 4,6-nonanedione, 1-phenyl-1,3-butanedione, 1-phenyl-2,4-pentanedione, 2,2,6,6-tetramethyl-heptane-3,5-dione, and the like.

The metal precursor can be synthesized in a reaction system by using raw materials for other metal precursors (for example, inorganic salts such as halides) and a compound selected from the group consisting of β-diketones, β-diketoimines, and β-diketimines.

Examples of the metal precursor include compounds, such as a $[M(A)(OZ)(OHZ)]_4$ cubane complex represented by the following general formula (15), which can synthesize a μ-oxo-dimer complex $[M(A)_x(OZ)(L)]_2$ in the present invention.

In the formula (15), Z represents a lower alkyl group which may have substituent(s), a lower alkoxy group which may have substituent(s), a lower alkenyl group which may have substituent(s), a lower alkynyl group which may have substituent(s), a halo-lower alkyl group which may have substituent(s), a halo-lower alkenyl group which may have substituent(s), a halo-lower alkynyl group which may have substituent(s), a cyclic hydrocarbon group which may have substituent(s), or a heterocyclic group which may have substituent(s).

In the present invention, examples of the lower alkyl group which may have substituent(s) include straight-chain or branched alkyl groups having 1 to 6 carbon atoms, such as a methyl group, an ethyl group, a propyl group, an isopropyl group, a 2,2-dimethylpropyl group, a 1-ethylpropyl group, a butyl group, an isobutyl group, a tert-butyl group, an isopentyl group, a pentyl group, and a hexyl group.

Examples of the lower alkoxy group which may have substituent(s) include straight-chain or branched alkoxy groups having 1 to 6 carbon atoms, such as a methoxy group, an ethoxy group, a propoxy group, an isopropoxy group, a butoxy group, a tert-butoxy group, a pentyloxy group, and a hexyloxy group.

Examples of the lower alkenyl group which may have substituent(s) include straight-chain or branched alkenyl groups having 2 to 6 carbon atoms, such as a vinyl group, a 1-propenyl group, a 2-propenyl group, a 2-butenyl group, a 1-butenyl group, a 3-butenyl group, a 2-pentenyl group, a 1-pentenyl group, a 3-pentenyl group, a 4-pentenyl group, a 1,3-butadienyl group, a 1,3-pentadienyl group, a 2-pentene-4-ynyl group, a 2-hexenyl group, a 1-hexenyl group, a 5-hexenyl group, a 3-hexenyl group, and a 4-hexenyl group.

Examples of the lower alkynyl group which may have substituent(s) include straight-chain or branched alkynyl groups having 2 to 6 carbon atoms, such as an ethynyl group, a 1-propynyl group, a 2-propynyl group, a 1-butynyl group, a 2-butynyl group, a 3-butynyl group, a 1-pentynyl group, a 2-pentynyl group, a 3-pentynyl group, a 4-pentynyl group, a 1-hexynyl group, a 2-hexynyl group, a 3-hexynyl group, a 4-hexynyl group, and a 5-hexynyl group.

Examples of the halo-lower alkyl group which may have substituent(s) include a fluoromethyl group, a difluoromethyl group, a trifluoromethyl group, a chloromethyl group, a dichloromethyl group, a trichloromethyl group, a 2-chloro-1,1-dimethylethyl group, and the like.

Examples of the halo-lower alkenyl group which may have substituent(s) include a chlorovinyl group, a dichlorovinyl group, a bromovinyl group, a fluorovinyl group, a chloropropenyl group, bromopropenyl group, a chlorobutenyl group, and the like.

Examples of the halo-lower alkynyl group which may have substituent(s) include a chloroethynyl group, a chloropropynyl group, a chlorobutynyl group, a chloropentynyl group, a bromoethynyl group, a bromopropynyl group, a bromobutynyl group, a bromopentynyl group, a fluoroethynyl group, and the like.

Examples of the cyclic hydrocarbon group which may have substituent(s) include a cyclopentyl group, a cyclohexyl group, a cycloheptyl group, a cyclooctyl group, a cyclohexenyl group, and the like.

Examples of the heterocyclic group which may have substituent(s) include a 2-furanyl group, a tetrahydro-2-furanyl group, a furfuryl group, a tetrahydrofurfuryl group, a thiofurfuryl group, a 2-pyranyl group, a tetrahydro-2-pyranyl group, a 2-pyranylmethyl group, a tetrahydro-2-pyranylmethyl group, and the like.

As the substituent which may be contained in Z, the same substituent as the substituent which may be contained in the aryl group in the above general formula (B) may be used.

M in the general formula (15) represents a fourth period transition metal. The fourth period transition metal is preferably manganese, iron, cobalt, nickel, or copper. The fourth period transition metal is further preferably manganese or cobalt. The fourth period transition metal is further preferably manganese.

A and x in the general formula (15) are the same as those in the following general formula (1).

[Chem. 6]

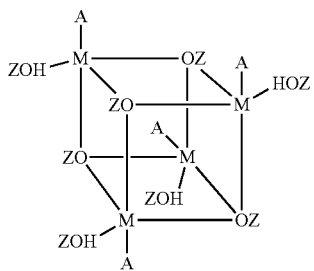

(15)

For example, the above [Mn(A)(OZ)(OHZ)]$_4$ cubane complex can be obtained by adding bases (for example, potassium ethoxide) to a solution containing halogenated manganese, and a ligand, which is selected from the group consisting of beta-diketonates, beta-diketoiminates, and beta-diketiminates.

The μ-oxo-dimer complex represented by the following general formula (1) in the present invention can be obtained by adding a nitrogen-containing compound or a phosphorus-containing compound to a metal complex having a ligand selected from the group consisting of beta-diketonates, beta-diketoiminates, and beta-diketiminates or to a carboxylate of the fourth period transition metal and allowing them to react in the presence of alcohol or alkoxide.

[Chem. 7]

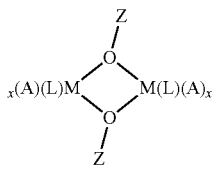

(1)

(In the formula (1),

M represents a fourth period transition metal;

A represents a carboxylic acid residue, a beta-diketonate, a beta-diketoiminate, or a beta-diketiminate;

in the case where A represents a carboxylic acid residue, x represents 2, and in the case where A represents a beta-diketonate, beta-diketoiminates, or beta-diketiminate, x represents 1;

L represents a nitrogen-containing compound or a phosphorus-containing compound; and Z represents a lower alkyl group which may have substituent(s), a lower alkoxy group which may have substituent(s), a lower alkenyl group which may have substituent(s), a lower alkynyl group which may have substituent(s), a halo-lower alkyl group which may have substituent(s), a halo-lower alkenyl group which may have substituent(s), a halo-lower alkynyl group which may have substituent(s), a cyclic hydrocarbon group which may have substituent(s), or a heterocyclic group which may have substituent(s).)

Production conditions for obtaining the μ-oxo-dimer complex represented by the above general formula (1) in the present invention are the same as the conditions in the above <Method for producing fourth period transition metal complex>.

A μ-oxo-bismanganese dimer complex [Mn(A)(OZ)(L)]$_2$ can be obtained by adding a ligand such as a nitrogen-containing compound or a phosphorus-containing compound to the [Mn(A)(OZ)(OHZ)]$_4$ cubane complex which is a metal precursor and heating them in toluene (in the following reaction formula (6), x, Z, A, and L are as defined in the above general formula (1), and y is as defined in the following reaction formula (7)).

[Chem 8]

(6)

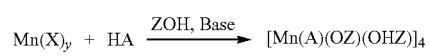

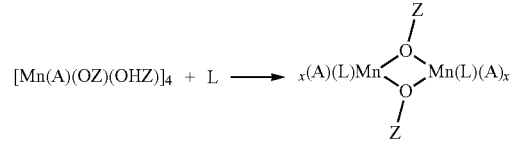

In addition, the μ-oxo-dimer complex [M(A)$_x$(OZ)(L)]$_2$ can be synthesized from other metal precursors having a fourth period transition metal. Namely, a nitrogen-containing compound or phosphorus-containing compound (L) is added to a fourth period transition metal complex M(A)$_y$ in which A represents a carboxylic acid residue, a beta (β)-diketonate, a beta (β)-diketoiminate, or a beta (β)-diketiminate, thereby forming a precursor M(L)(A)$_y$ in which the nitrogen-containing compound or phosphorus-containing compound is coordinated with the fourth period transition metal atom.

Further, alcohol (ZOH) or alkoxylate (ZO$^-$) is added, and then, the μ-oxo-dimer complex [M(A)$_x$(OZ)(L)]$_2$ in the present invention in which oxygen atoms are crosslinked with the two fourth period transition metal complexes M is obtained.

[Chem. 9]

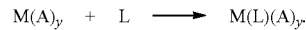

(7)

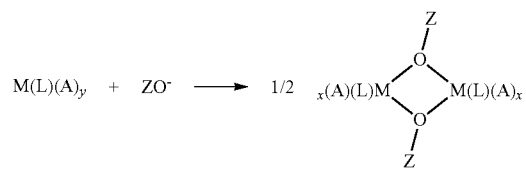

In the above reaction formula (7), x, M, Z, A, and L are as defined in the above general formula (1).

In the case where A represents a carboxylic acid residue, y represents 2; and in the case where A represents a beta-diketonate, beta-diketoiminate, or beta-diketiminate, which is a bidentate ligand, y represents 2 or 3.

In the case of a dinuclear complex [M(A)$_x$(OZ)(L)]$_2$ having a fourth period transition metal, x represents 1 in a case where y represents 2 or 3.

When the above μ-oxo-dimer complex is used, an amide compound can be converted into an ester compound easily. Therefore, it is clear that the present catalyst is involved in this reaction.

After the fourth period transition metal complex, which is prepared in advance as described above, is prepared as a catalyst, the catalyst may be added to a reaction. In addition, after a metal precursor and a nitrogen-containing compound or a phosphorus-containing compound in an alcohol that are raw materials of an ester compound are appropriately added to an amide compound that is a raw material, the reaction can proceed by stirring the mixture at a temperature of the reaction conditions.

The usage amount of the catalyst formed of the fourth period transition metal complex in the present invention is not particularly limited, and the amount of fourth period transition metal atoms is generally 0.001 mol to 0.9 mol, more preferably 0.001 mol to 0.3 mol, and still more preferably 0.01 mol to 0.1 mol, relative to 1 mol of the raw material in each reaction.

The reaction conditions in each reaction are not particularly limited, and each reaction can be performed even under mild neutral conditions.

<Alcohols>

In the present invention, alcohols to be used are not particularly limited, and various kinds of alcohols may be used, and the alcohols may be any of primary alcohols, secondary alcohols, and tertiary alcohols. In addition, the alcohols may be any of monohydric alcohols, dihydric alcohols, and polyhydric alcohols having three or more hydroxyl groups.

The number of carbon atoms of the alcohols is, for example, 1 to 30, preferably 1 to 20, and more preferably 1 to 10. In addition, the alcohols may have substituent(s) (functional group) on a carbon skeleton. Examples of the substituent which may be contained include halogen atoms (fluorine atoms, chlorine atoms, bromine atoms, iodine atoms, or the like), alkyl groups having 1 to 6 carbon atoms, alkoxy groups having 1 to 4 carbon atoms (a methoxy group, an ethoxy group, a propoxy group, a butoxy group, or the like), amino groups, and the like.

In addition, the alcohols may have one or two or more cyclic skeletons in a molecule. Examples of the ring constituting the cyclic skeleton includes a monocyclic or polycyclic non-aromatic or aromatic ring.

Examples of the monocyclic non-aromatic ring include 3- to 15-membered cycloalkane rings such as a cyclopentane ring, a cyclohexane ring, a cyclooctane ring, and a cyclodecane ring, 3- to 15-membered cycloalkene rings such as a cyclopentene ring and a cyclohexene ring, and the like.

Examples of the polycyclic non-aromatic ring include an adamantane ring, a norbornane ring, and the like.

Examples of the monocyclic or polycyclic aromatic ring include aromatic carbocyclic rings such as a benzene ring, a naphthalene ring, a pyridine ring, and a quinoline ring, and aromatic heterocycles (for example, an aromatic heterocycle having at least one kind of hetero atom selected from an oxygen atom, a nitrogen atom, and a sulfur atom, or the like).

Representative examples of alcohols include the aliphatic alcohols, alicyclic alcohols, and alcohols having aromatic rings.

Examples of the aliphatic alcohols (including those having a substituent) include amino alcohols, methanol, ethanol, 1-propanol, 2-propanol, 1-butanol, 2-butanol, tert-butyl alcohol, amyl alcohol, tert-amyl alcohol, 1-hexanol, 2-hexanol, 1-octanol, 2-ethyl-1-hexanol, isodecyl alcohol, lauryl alcohol, cetyl alcohol, stearyl alcohol, ethylene glycol, 1,3-butanediol, trimethylolpropane, and the like.

Examples of the alicyclic alcohols include cyclopentanol, cyclohexanol, methyl cyclohexanol, dimethyl cyclohexyl alcohol, cyclohexenyl alcohol, adamantanol, adamantane methanol, 1-adamantyl-1-methylethyl alcohol, 1-adamantyl-1-methylpropyl alcohol, 2-methyl-2-adamantanol, 2-ethyl-2-adamantanol, and the like.

Examples of alcohols having aromatic rings (including those having a substituent) include benzyl alcohol, methylbenzyl alcohol, 1-phenylethanol, 2-phenylethanol, and the like.

Examples of the amino alcohols include dimethyl ethanolamine, diethyl ethanolamine, dipropylethanolamine, 6-aminohexanol, trans-4-aminocyclohexanol, prolinol, and the like.

In the present invention, methanol, ethanol, tert-butyl alcohol, cyclohexanol, benzyl alcohol are preferred. Among them, methanol and ethanol are preferred, and methanol is particularly preferred.

<Amide Compound>

In the present invention, the tertiary amide compound to be used is not particularly limited, and various kinds of amide compounds may be used. An N,N-dialkylamide compound is particularly preferred.

Examples of the amide compound include compounds represented by the following general formula (8).

[Chem. 10]

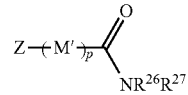

(8)

In the above general formula (8), Z is as defined in the above general formula (1).

M' represents a linker moiety and is a divalent atomic group. Examples of the divalent atomic group represented by M' include straight-chain or branched alkylene groups having 1 to 20 carbon atoms, cycloalkylene groups having 3 to 8 carbon atoms, alkenylene groups having 2 to 20 carbon atoms, alkynylene groups having 2 to 20 carbon atoms, arylene groups having 6 to 20 carbon atoms, aralkylene groups having 7 to 20 carbon atoms, heteroalkylene groups having 1 to 20 carbon atoms, heteroarylene groups having 2 to 20 carbon atoms, heteroaralkylene groups having 3 to 20 carbon atoms, phenylenebisalkylene groups having 8 to 20 carbon atoms, phenylenebisvinylene groups having 8 to 20 carbon atoms, polyfluorene groups, polythiophene groups, dialkylsilanediyl groups and groups derived from derivatives thereof.

These divalent atomic groups may have substituent(s), and two or more of these atomic groups may be combined.

p represents 0 or 1.

In the general formula (8), each of $R^{26}$ and $R^{27}$ is represented by the following general formula (9).

[Chem. 11]

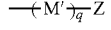

(9)

In the above general formula (9), M' has the same definition as M' in the general formula (8).

q represents 0 or 1.

Z has the same definition as Z in the above general formula (8).

Alternatively, $R^{26}$ and $R^{27}$ may be bonded to each other to form a nitrogen-containing heterocycle together with the adjacent nitrogen atom.

<Conversion Reaction in the Present Invention>

An N,N-dialkylamide compound can be converted into an ester compound by using the fourth period transition metal complex in the present invention as a catalyst.

In addition, by using the fourth period transition metal complex of the present invention as a catalyst, an amine can react with a carboxylic acid ester to perform amidation, and a transesterification reaction can be performed.

The addition amount of the catalyst is, for example, 0.01 mol to 10 mol, and preferably 0.1 mol to 5 mol relative to 1 mol of the starting material.

The amidation reaction between the amine and the carboxylic acid ester can be performed by a common method. For example, a mixture of an amine and a carboxylic acid ester may be heated at a temperature of, for example, from 20° C. to 250° C., preferably from 50° C. to 200° C.

Examples of the amine include the aliphatic amines and aromatic amines, which are described above.

Examples of the carboxylic acid ester include methyl acetate, ethyl acetate, methyl propionate, ethyl propionate, methyl butyrate, methyl isobutyrate, trimethyl methyl acetate, and the like.

The fourth period transition metal complex in the present invention may also be used for a reaction of converting an amide compound to another amide compound, or a reaction of converting an ester compound to another ester compound, in addition to the reaction of converting an amide compound to an ester compound.

In the present invention, a primary amide compound or a secondary amide compound can be converted into an ester compound, and an esterification reaction proceeds even with a tertiary amide compound, which is difficult to proceed under neutral conditions.

The tertiary-amide amide compound refers to an amide compound in which two amide nitrogen groups are bonded to a group selected from an alkyl group, an aryl group, and a heteroaryl group. Examples of the tertiary-amide compound include N-alkyl-N-arylamide compounds such as an N,N-dialkylamide compound and an N-methyl-N-phenyl-amide compound, and the like.

The reaction in the present invention may be performed by any method of a batch type, a semi-batch type, and a continuous type. In any of the case where an amide compound and alcohols are added to a reaction system in this order and the case where alcohols and amides are added in this order, ingredients to be added may be added sequentially, or may be added intermittently.

The reaction time in the method of the present invention is not particularly limited, and is generally about 1 hour to 45 hours, and preferably about 6 hours to 18 hours.

The reaction temperature is not particularly limited, and is from room temperature to about 180° C., preferably from 50° C. to 150° C., and more preferably about 80° C. to 150° C. These conditions are appropriately changed depending on the kinds and amounts of used raw materials and the like. The reaction in the present invention can also be performed at a reaction temperature at which the amine as a by-product or the target ester produced can be continuously separated from the reaction system.

As a solvent used for the reaction in the present invention, any solvent may be used as long as it does not affect the fourth period transition metal complex in the present invention. The alcohols as a raw material used for the transesterification reaction may be used as a solvent.

The present reaction can be performed under the atmosphere, in the air, or under an inert gas atmosphere such as nitrogen gas and argon gas, and is preferably performed under the inert gas atmosphere.

The reaction may be implemented while the amine as a by-product or the target ester produced can be continuously separated from the reaction system. In particular, by separating the amine as a by-product, the conversion into the ester compound can be promoted. As a method for separation, for example, extraction, distillation (azeotropic distillation, etc.), rectification, molecular distillation, adsorption, crystallization, recrystallization, column chromatography, or the like can be used. Separation and purification can be easily performed by a separation method combining the above separation methods.

In addition, by using a capturing agent (scavenger), the amine as a by-product can be removed, and the reaction can also be promoted. Examples of the capturing agent include polymers having an aldehyde group, polymer having an isocyanate group, polymers having a sulfonic acid, a silica gel carrier, and the like, but the capturing agent is not limited to these examples.

After the reaction in the present invention, the obtained ester may be directly applied for the next use, or may be used after purification. As a method for purification, a common method such as extraction, distillation, rectification, molecular distillation, adsorption, and crystallization may be used. The purification may be performed in a continuous manner, or may be performed in a discontinuous manner (batch type).

Figure 9:
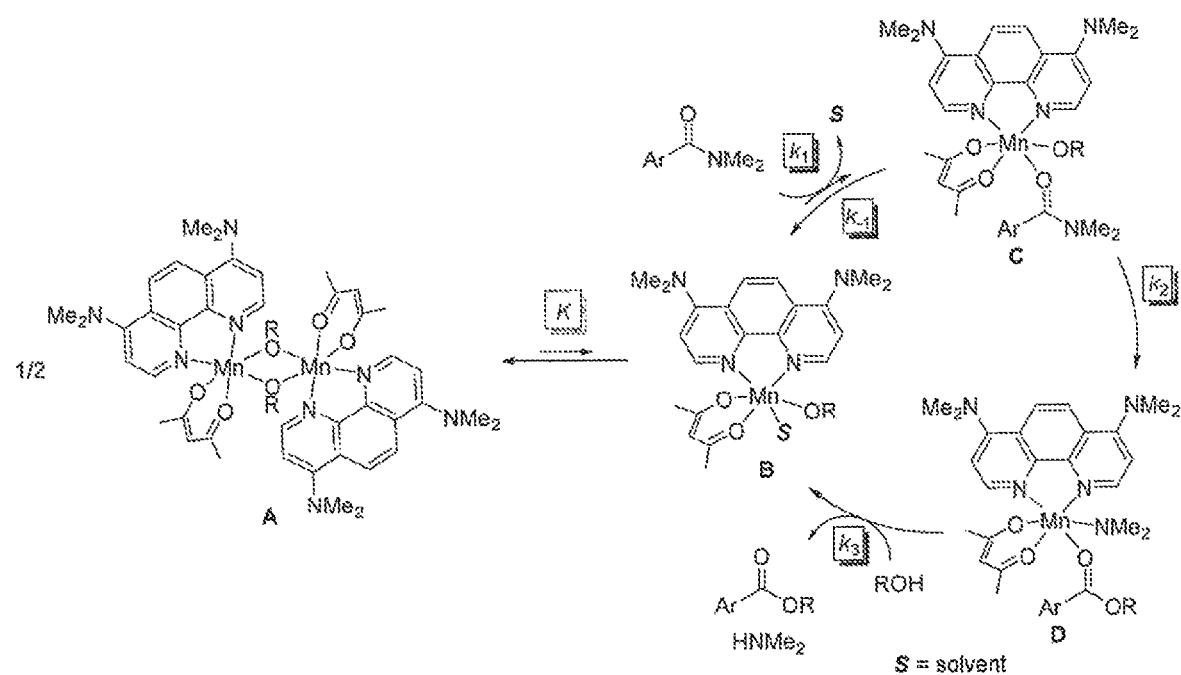
FIG. 9 shows a putative reaction mechanism of a reaction of converting an amide compound into an ester compound in the present invention.

FIG. 9 shows a putative reaction mechanism of a reaction of converting an amide compound into an ester compound in the present invention. An inert alkoxy-crosslinked binuclear complex, that is, a μ-oxo-dimer complex is in equilibrium with a mononuclear complex which is active due to coordination of a solvent, that is, an alkoxide mononuclear complex. It is presumed that, in the case where an amide compound exists, the amide compound coordinates with a manganese metal atom of a mononuclear complex, and further a reaction in which the amide compound cleaves and is exchanged with an alkoxide coordinated with the manganese complex occurs, thereby generating an ester compound. The present reaction is considered to proceed catalytically by discharging dimethylamine from the system.

EXAMPLES

Hereinafter, the present invention is described in detail with reference to Examples and Comparative Examples, but the present invention is not limited thereto. The analytical instruments used are as follows. All operations in Examples and Comparative Examples were performed under the argon atmosphere.

The nuclear magnetic resonance measurement was performed by using a nuclear magnetic resonance device Bruker AV 400 under the conditions of 400 MHz ($^1$H-NMR), 100 MHz ($^{13}$C-NMR), and 376 MHz ($^{19}$F-NMR). All $^1$H-NMR chemical shifts were determined from peaks of deuterium atoms remaining in a solvent at 7.26 ppm ($CDCl_3$), 5.32 ppm ($CD_2Cl_2$), and 2.50 ppm (DMSO-$d_6$). All $^{13}$C($^1$H)-NMR chemical shifts were determined from peaks of carbon atoms in a solvent at 77.16 ppm ($CDCl_3$), 53.84 ppm ($CD_2Cl_2$), and 39.52 ppm (DMSO-$d_6$). All $^{19}$F-NMR chemical shifts were determined to the external reference α,α,α-trifluorotoluene at δ −63.9.

Gas chromatography (GC) measurement was performed by using gas chromatograph Shimadzu GC-2014 and using J&W Scientific DB-5 or Shimadzu SH-Rtx-50 as a column.

Isolation/purification was performed by flash column chromatography in which silica gel 60 (0.040-0.063 mm, 230-400 mesh ASTM) was used.

X-ray single crystal structure analysis was performed by emitting Mo-Kα rays (0.71075 Å) using a single crystal X-ray diffractometer equipped with hybrid pixel detector (Rigaku XtaLAB P200 system). The crystals were mounted on a CryoLoop (Hampton Research Corp.) together with high-viscosity liquid paraffin and measurement was performed while performing cooling with 113 (1) K nitrogen vapor. Crystal structure determination was performed by using a program SHELXL-2013.

The operations, in which compounds unstable to the air and the moisture were used, were all performed using a normal Schlenk technique, or performed in a glove box under argon.

[Examples 1 to 5, Comparative Examples 1 to 10]
Conversion Reaction from 2-Naphthoic Acid Amide (1a) to 2-Naphthoic Acid Ester (2a) Using Various Metal Precursors

[Chem. 12]

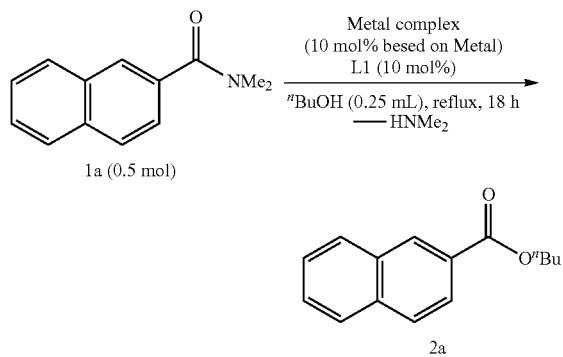

To 0.50 mmol of 2-naphthoic acid amide (1a) and 0.25 mL of 1-butanol, 10 mol % of various metal precursors shown in Table 1 and 10 mol % of 2,2'-bipyridine [ligand (L1)] were added, and the reaction was performed at a reflux temperature for 18 hours while discharging dimethylamine as a by-product from a reaction system.

A yield of 2-naphthoic acid ester (2a) at that time was measured by an internal standard method using dodecane and gas chromatography (GC). The reaction results of Examples 1 to 5 and Comparative Examples 1 to 10 are shown in Table 1. In Examples 2 and 4, each of the addition amount of the metal precursor and the addition amount of the ligand (L1) was 1 mol %, and reactions were performed.

TABLE 1

|  |  | Metal precursor | Yield [%] |
|---|---|---|---|
| Examples | 1 | Mn(acac)$_3$ | 99 |
|  | 2 | Mn(acac)$_3$ (* 1 mol %) | 90 |
|  | 3 | Mn(acac)$_2$ | >99 |
|  | 4 | Mn(acac)$_2$ (* 1 mol %) | 85 |
|  | 5 | Mn(acac)$_2$ hydrate | 84 |

TABLE 1-continued

|  |  | Metal precursor | Yield [%] |
|---|---|---|---|
| Comparative Examples | 1 | Fe(acac)$_2$ | 22 |
|  | 2 | Fe(acac)$_2$ | 18 |
|  | 3 | Co(acac)$_2$ | 18 |
|  | 4 | Co(acac)$_3$ | 17 |
|  | 5 | Ni(acac)$_2$ | 16 |
|  | 6 | Cu(acac)$_2$ | trace |
|  | 7 | Zn(acac)$_2$ | 10 |
|  | 8 | Cr(acac)$_3$ | n.d. |
|  | 9 | V(acac)$_3$ | n.d. |
|  | 10 | Sc(acac)$_3$ hydrate | trace |

In the case where manganese acetylacetonate [Mn(acac)$_3$] was used as a metal precursor, 2-naphthoic acid ester (2a) was obtained quantitatively (Example 1).

In the case where each of the addition amounts of manganese acetylacetonate [Mn(acac)$_3$] and 2,2'-bipyridine [ligand (L1)] was 1 mol %, 2-naphthoic acid ester (2a) was obtained with a yield of 90% (Example 2).

In the case where manganese acetylacetonate [Mn(acac)$_2$] having an oxidation number different from that of Example 1 was used, 2-naphthoic acid ester (2a) was obtained quantitatively (Example 3).

In the case where each of the addition amounts of manganese acetylacetonate [Mn(acac)$_2$] having an oxidation number different from that of Example 1 and 2,2'-bipyridine [ligand (L1)] was 1 mol %, 2-naphthoic acid ester (2a) was obtained with a yield of 85% (Example 4).

In the case where hydrated manganese acetylacetonate [Mn(acac)$_2$] was used, 2-naphthoic acid ester (2a) was obtained with a yield of 84% (Example 5).

On the other hand, Fe (II), Fe (III), Co (II), Co (III), Ni (II), Cu (II), Zn (II), Cr (III), V (III), and Sc (III) were used to carry out studies of the reaction, and yields of 2-naphthoic acid ester (2a) in all the cases were 20% or less (Comparative Examples 1 to 10).

In Table 1, "n.d." means non-detection and "trace" means a very small amount.

As described above, a manganese complex gave good results as a metal precursor as compared with other metal complexes.

[Examples 6 to 32] Conversion Reaction from 2-Naphthoic Acid Amide (1a) to 2-Naphthoic Acid Ester (2a) Using Various Ligands

[Chem. 13]

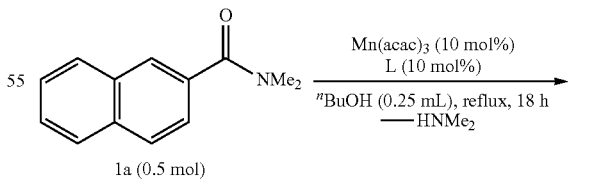

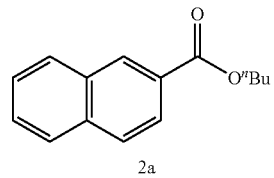

A reaction was performed in the same method as Example 1 except that the ligand (L1) in Example 1 was changed to ligands shown in Table 2. The yield was measured by an internal standard method using gas chromatography (GC) in the same manner as Example 1. The reaction results of Examples 6 to 32 are shown in Table 2.

TABLE 2

| Examples | Ligands | Yield [%] |
|---|---|---|
| 6 | L2 | 93 |
| 7 | L3 | 80 |
| 8 | L4 | 89 |
| 9 | L5 | 38 |
| 10 | L6 | 62 |
| 11 | L7 | 47 |
| 12 | L8 | 96 |
| 13 | L9 | 99 |
| 14 | L10 | 95 |
| 15 | L11 | >99 |
| 16 | L12 | 97 |
| 17 | L13 | 2 |
| 18 | L14 | 78 |
| 19 | L15 | 4 |
| 20 | L16 | 16 |
| 21 | L17 | 76 |
| 22 | L18 | 68 |
| 23 | L19 | 78 |
| 24 | L20 | 93 |
| 25 | L21 | 64 |
| 26 | L22 | 51 |
| 27 | L23 | 74 |
| 28 | L24 | 65 |
| 29 | L25 | 66 |
| 30 | L26 | 38 |
| 31 | L27 | 71 |
| 32 | L28 | 68 |
| — | | |

[Chem. 14]

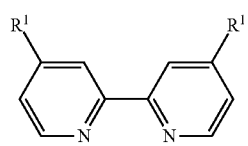

L1: $R^1$ = H
L2: $R^1$ = Me
L3: $R^1$ = $^t$Bu
L4: $R^1$ = OMe
L5: $R^1$ = COOMe

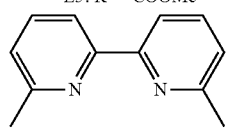

L6

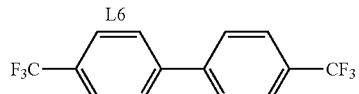

L7

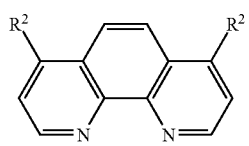

L8: $R^2$ = H
L9: $R^2$ = Me
L10: $R^2$ = OMe
L11: $R^2$ = NMe$_2$
L12: $R^2$ = Ph
L13: $R^2$ = Cl

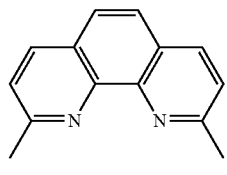

L14

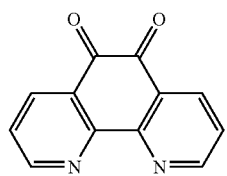

L15

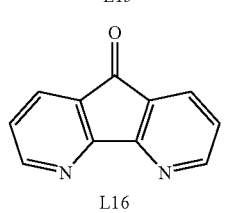

L16

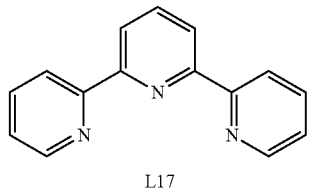

L17

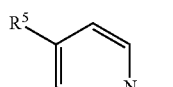

L18: $R^5$ = H
L19: $R^5$ = Me
L20: $R^5$ = NMe$_2$
L21: $R^5$ = CN

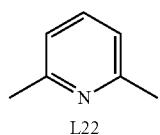

L22

L23: $R^6$ = NMe$_2$
L24: $R^6$ = NH$_2$
L25: $R^6$ = OMe
L26: $R^6$ = PPh$_2$

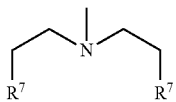

L27: R⁷ = NMe$_2$

P(3,5—Me$_2$C$_6$H$_3$)$_3$

L28

In the case where 2,2'-bipyridine derivatives [ligands (L2) to (L7)] were used, high activity was obtained in the case of ligands (L2) to (L4) having an electron donating group at the 4- and 4'-positions.

In contrast, since catalytic activity decreased in the case of a ligand (L6) having a methyl group at the 6- and 6'-positions, the present reaction is considered to be difficult to proceed when a bulky ligand is used.

In the case where ligands (L5) and (L7) having an electron withdrawing group were used, the catalytic activity significantly decreased, and thus 2-naphthoic acid esters (2a) were obtained with yields of 38% and 47%, respectively (Examples 6 to 11).

As a result of studies using 1,10-phenanthroline [ligand (L8)] having a skeleton similar to bipyridine and its derivatives (L9) to (L14), the effects of the electronic and steric environments of the ligand on the activity tend to be the same as those of the bipyridine derivatives, and high activity was exhibited in the case where a ligand having an electron donating group was used.

In contrast, activity decreased in the case of a ligand (L13) having a chloro group, which is an electron-withdrawing group, and a ligand (L14) having a methyl group at the 2- and 9-positions. In particular, reactions proceeded quantitatively in the case of 1,10-phenanthroline having a methyl group at the 4- and 7-positions [ligand (L9)], and 1,10-phenanthroline having a diamino group at the 4- and 7-positions [ligand (L11)]. As a result, it was found that the reaction was promoted by using a ligand having an electron donating group at the 4- and 7-positions (Examples 12 to 18).

In addition, in the case where a ligand (L15) or (L16) having a bipyridine skeleton was used, catalytic activity remained extremely low since the ligand (L15) or (L16) has a carbonyl group which is an electron withdrawing group (Examples 19 and 20).

In the case where terpyridine [ligand (L17)] was used as a tridentate ligand, the yield was 76%. In the case where pyridine [ligand (L18)] and its derivative ligands (L19) to (L22) were used as monodentate ligands in two equivalents relative to the catalyst, high activity was observed in the case of DMAP (N,N-dimethyl-4-aminopyridine) [ligand (L22)] having a dimethylamino group at the 4-position, but the yields were low in the case where other ligands were used (Examples 21 to 26).

In the case where bidentate alkylamine ligands (L23) and (L24), bis(diphenylphosphino)ethane (dppe) [ligand (L26)] as a phosphorus-containing compound, a bisaminoalkylamine tridentate ligand (L27), and a ligand (L28) as an aminophosphine compound were used, it was confirmed that an ester compound was obtained (Examples 27 to 32).

As described above, it was found that 1,10-phenanthroline having an electron donating group at 4- and 7-positions gave the best results as a ligand.

[Examples 33 to 38] Conversion Reaction from 2-Naphthoic Acid Amide (1a) to 2-Naphthoic Acid Ester (2a) when Addition Amounts of Ligand and Metal Precursor are Changed

[Chem. 15]

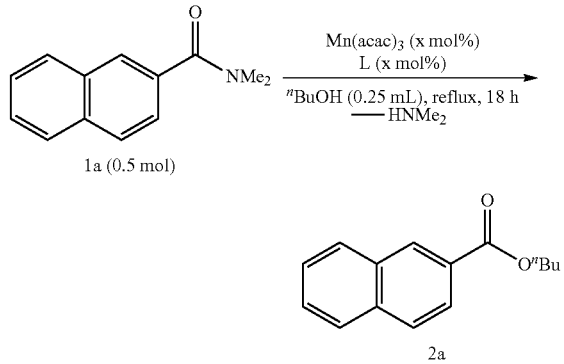

Reactions were performed in the same method as Example 1 except that the ligand (L1), the addition amounts of manganese acetylacetonate [Mn(acac)$_3$] and ligands, and the kinds of ligands in Example 1 were changed as shown in Table 3. The yield was measured by an internal standard method using gas chromatography (GC) in the same manner as Example 1. The reaction results of Examples 33 to 38 are shown in Table 3.

TABLE 3

| Examples | Addition amount x [mol %] | Ligands | Yield [%] |
|---|---|---|---|
| 33 | 5 | L9 | 96 |
| 34 | 5 | L11 | >99 |
| 35 | 4 | L11 | 96 |
| 36 | 3 | L11 | 97 |
| 37 | 2 | L11 | 91 |
| 38 | 1 | L11 | 90 |

As a result, in the case of 1,10-phenanthroline having a diamino group at the 4- and 7-positions [ligand (L11)], a yield of 90% was obtained even if the addition amount of the metal precursor was lowered to 1 mol %, and the best results were obtained.

[Examples 39 to 41] Studies on Combinations of Metal Precursor and Ligand

[Chem. 16]

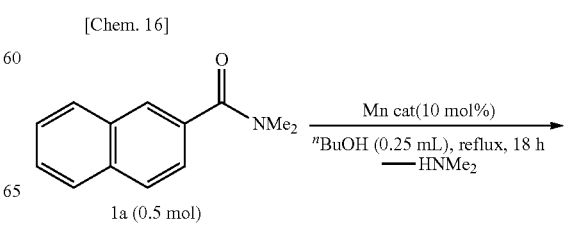

-continued

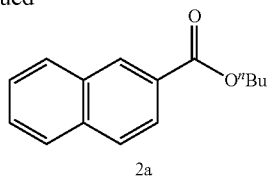

2a

Reactions were performed in the same method as Example 1 except that a combination of 1,10-phenanthroline [ligand (L8)] and bis(dipivaloylmethanate)manganese [Mn(dpm)$_2$] or tris(dipivaloylmethanate) manganese [Mn(dpm)$_3$] shown in Table 4 was used instead of the combination of manganese acetylacetonate [Mn(acac)$_3$] and the ligand (L1) in Example 1. The yield was derived by using $^1$H-NMR with phenanthrene as an internal standard. The reaction results and the kinds and amount of by-products in Examples 39 to 41 are shown in Table 4.

"Mn(dpm)$_2$ (L8)" in Example 41 is one metal complex, and Example 41 shows that a reaction proceeded from "Mn(II)(dpm)$_2$ and L8" to an "active complex" via "Mn(dpm)$_2$ (L8)" in the system.

TABLE 4

| Examples | Combinations | Yield [%] | Amount of by-products [μmol] | | |
| --- | --- | --- | --- | --- | --- |
| | | | Butyl pivalate | Pinacoline | Dpm-H |
| 39 | Mn(II)(dpm)$_2$ + L8 | 96 | 13.8 | 2.32 | 24.4 |
| 40 | Mn(II)(dpm)$_3$ + L8 | >99 | 62.5 | 26.9 | 55.2 |
| 41 | Mn(dpm)$_2$ (L8) | 96 | 31.0 | 3.71 | 33.0 |

[Examples 42 to 55] Studies on Metal Precursor

[Chem. 17]

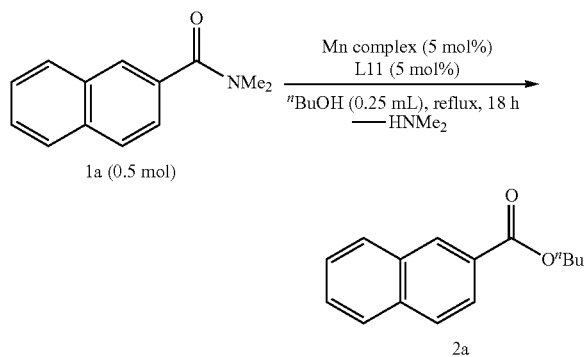

Reactions were performed in the same method as Example 1 except that the metal precursor in Example 1 was changed as shown in Table 5, and the ligand (L11) was used instead of the ligand (L1). The yield was measured by an internal standard method using gas chromatography (GC) in the same manner as Example 1. The reaction results of Examples 42 to 55 are shown in Table 5. In Examples 46, 48, 50, and 53, each of the addition amount of the metal precursor and the addition amount of the ligand (L11) was 1 mol %, and reactions were performed.

TABLE 5

| Examples | Metal precursors | Yield [%] |
| --- | --- | --- |
| 42 | Mn(OAc)$_3$ hydrate | 71 |
| 43 | Mn(OAc)$_2$ | 95 |
| 44 | Mn(OAc)$_2$ hydrate | 84 |
| 45 | Mn(acac)$_3$ | >99 |
| 46 | Mn(acac)$_3$ (* 1 mol %) | 90 |
| 47 | Mn(acac)$_2$ | 99 |
| 48 | Mn(acac)$_2$ (* 1 mol %) | 85 |
| 49 | Mn(acac)$_2$ hydrate | >99 |
| 50 | Mn(acac)$_2$ hydrate (* 1 mol %) | 90 |
| 51 | Mn(dpm)$_3$ | 30 |
| 52 | Mn(dpm)$_2$ | >99 |
| 53 | Mn(dpm)$_2$ (* 1 mol %) | 55 |
| 54 | Mn(hfac)$_2$ | 83 |
| 55 | Mr(hfac)$_2$ hydrate | 15 |

[Examples 56 to 65] Studies on Amide as Raw Material

[Chem. 18]

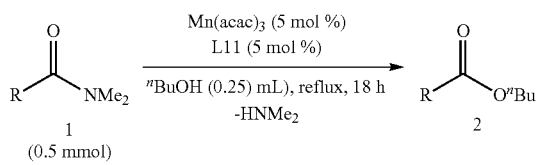

Reactions were performed in the same method as Example 1 except that the amide as a raw material (2-naphthoic acid amide (1a)) in Example 1 was changed to the above compound 1 having a substituent R shown in Table 6, the ligand (L11) was used instead of the ligand (L1), and each of the addition amount of Mn(acac)$_3$ and the addition amount of the ligand was 5 mol %. The yield was measured by an internal standard method using gas chromatography (GC) in the same manner as Example 1. The reaction results of Examples 56 to 65 are shown in Table 6.

TABLE 6

| Examples | R | Yield [%] |
| --- | --- | --- |
| 56 | Phenyl | 92 |
| 57 | p-Tolyl | 78 |
| 58 | m-Tolyl | 60 |
| 59 | p-OMeC$_6$H$_4$ | 83 |
| 60 | P-CNC$_6$H$_4$ | 53 |
| 61 | p-BrC$_6$H$_4$ | 89 |
| 62 | p-ClC$_6$H$_4$ | 94 |
| 63 | p-IC$_6$H$_4$ | 90 |
| 64 | 4-pyridyl | 91 |
| 65 | 2-furyl | 84 |

[Examples 66 to 70] Studies on Amide as Raw Material

[Chem. 19]

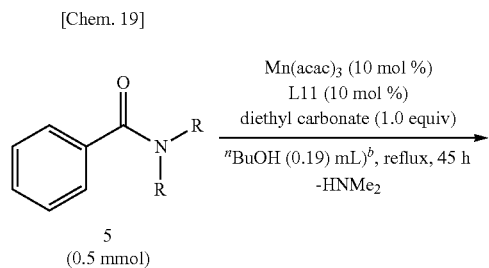

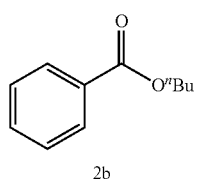

Reactions were performed in the same method as Example 1 except that the amide as a raw material (2-naphthoic acid amide (1a)) in Example 1 was changed to substances having a variety of substituents on a nitrogen atom as shown in Table 7, each of the addition amount of Mn(acac)$_3$ and the addition amount of the ligand (L11) was 10 mol %, and 1.0 equivalent of diethyl carbonate was used. The yield was measured by an internal standard method using gas chromatography (GC) in the same manner as Example 1. The results of Examples 66 to 70 are shown in Table 6.

TABLE 7

| Examples | Amide as raw material | Yield [%] |
|---|---|---|
| 66 | | 77 |
| 67 | | 81 |
| 68 | | 27 |
| 69 | | 94 |

TABLE 7-continued

| Examples | Amide as raw material | Yield [%] |
|---|---|---|
| 70 | | 87 |

[Application Examples 1 to 4] Application to Deprotection of Amides

[Chem. 20]

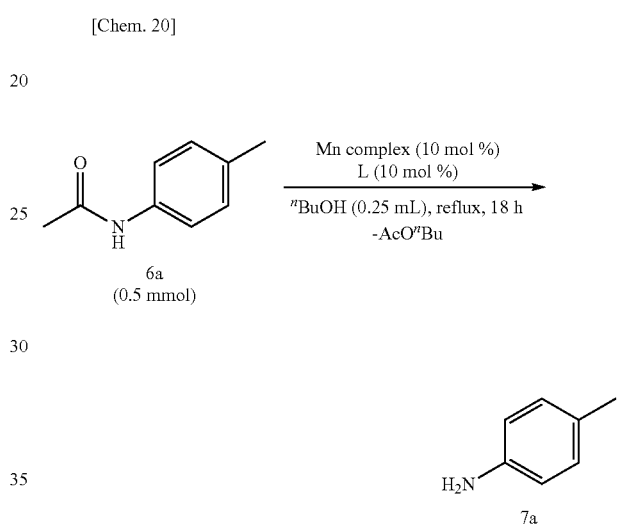

Reactions were performed in the same method as Example except that the amide as a raw material (2-naphthoic acid amide (1a)) in Example 1 was changed to the compound 6a of the above formula, and the metal precursor and the ligand were changed to those shown in Table 8, and the application of the present catalytic reaction to the deprotection of acetamide was examined. The yield of the compound 7a in the above formula was measured by an internal standard method using gas chromatography (GC) in the same manner as Example 1. The reaction results of Application Examples 1 to 4 are shown in Table 8.

TABLE 8

| Application Examples | Metal precursors | Ligands | Yield [%] |
|---|---|---|---|
| 1 | Mn(acac)$_3$ | L8 | 53 |
| 2 | Mn(acac)$_3$ | L11 | 57 |
| 3 | Mn(dpm)$_2$ | L8 | 59 |
| 4 | Mn(dpm)$_2$ | L11 | 61 |

Regarding the deacylation reaction, the combinations of Mn(acac)$_3$ or Mn(dpm)$_2$ with 1,10-phenanthroline [ligand (L8)] or 1,10-phenanthroline having a diamino group at the 4- and 7-positions [ligand (L11)] were studied. As a result, the combination of Mn(dpm)$_2$ and 1,10-phenanthroline having a diamino group at the 4- and 7-positions [ligand (L11)] showed the highest activity.

[Examples 71 to 76] Studies on Alcohols

[Chem. 21]

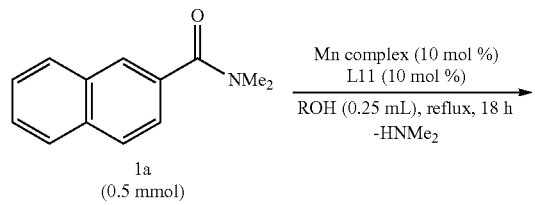

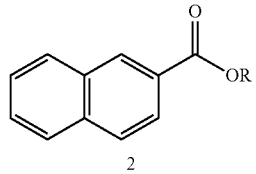

Reactions were performed in the same method as Example 1 except that the ligand (L1) in Example 1 was changed to 1,10-phenanthroline having a diamino group at the 4- and 7-positions [ligand (L11)], and 1-butanol was changed to alcohols shown in Table 9. The yield was derived from an isolation yield. The reaction results of Examples 71 to 76 are shown in Table 9. However, in Example 73, 0.25 mL of toluene was added and the reaction was performed.

TABLE 9

| Examples | Alcohols | Yield [%] |
|---|---|---|
| 71 | 1-propanol | 61 |
| 72 | 2-pentanol | 43 |
| 73 | 4-methylbenzyl alcohol | 77 |
| 74 | 3-pentanol | 38 |
| 75 | 4-heptanol | 73 |
| 76 | cyclohexanol | 28 |

[Example 77] Studies on Transesterification Reaction

[Chem. 22]

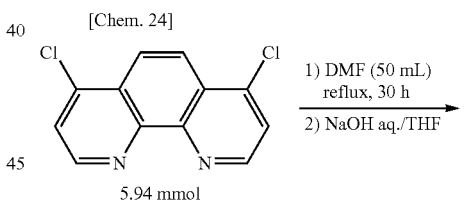

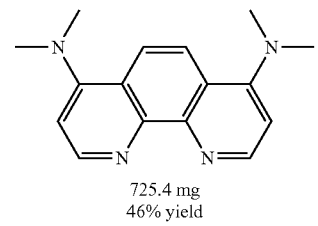

Studies on the transesterification reaction were performed by using manganese acetylacetonate Mn(acac)$_3$ and bis (dipivaloyl methanate) manganese Mn(dpm)$_2$, and 1,10-phenanthroline [ligand (L8)], and using methyl benzoate as a substance.

Specifically, 10 mol % of manganese acetylacetonate [Mn(acac)$_3$] and 10 mol % of 1,10-phenanthroline [ligand (L8)] were added to 0.500 mmol of methyl benzoate and 0.250 mL of 1-butanol, and the reaction was performed at a reflux temperature for 18 hours.

All the methyl benzoate was consumed, and corresponding esters were obtained at a NMR yield of 93%.

[Example 78] Studies on Transesterification Reaction

[Chem. 23]

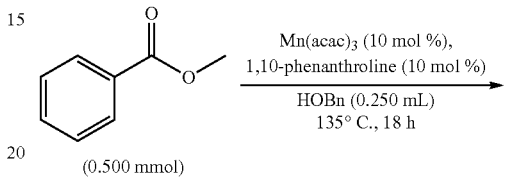

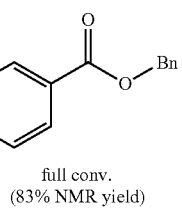

A reaction was performed in the same manner as Example 77 except that 1-butanol was changed to benzyl alcohol.

All the methyl benzoate was consumed, and corresponding esters were obtained at a NMR yield of 83%.

[Synthesis Example 1] Synthesis of Ligand (L11)

[Chem. 24]

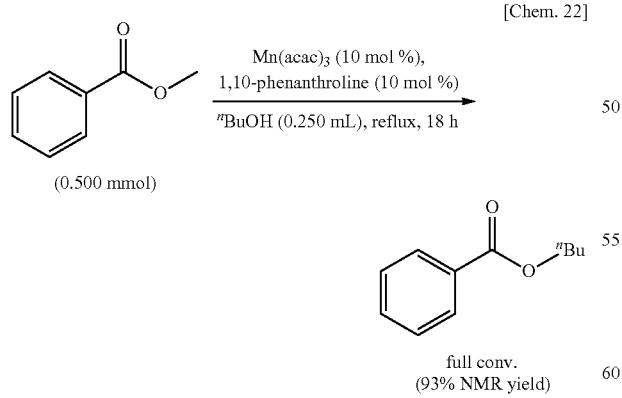

A suspension of 4,7-dichloro-1,10-phenanthroline (1.48 g, 5.94 mmol) in N,N-dimethylformamide (50 mL) was heated to reflux for 30 hours under an argon atmosphere. The reaction mixture was slowly cooled to reach a room temperature, and then the solvent was distilled off under reduced pressure. The obtained residue was dissolved in 1 mol/L of a sodium hydroxide aqueous solution (50 mL) and tetrahydrofuran (70 mL), and extraction was performed with dichloromethane (50 mL) for three times. A recovered organic layer was washed with 1 mol/L of a sodium hydroxide aqueous solution (50 mL) for two times and washed with saturated saline (50 mL), and a solvent was distilled off. The obtained solid was washed with ethyl acetate, and 725.4 mg of ligand (L11) was obtained as a purple solid with a yield of 46%.

[Example 79] Synthesis of Manganese Complex

[Chem. 25]

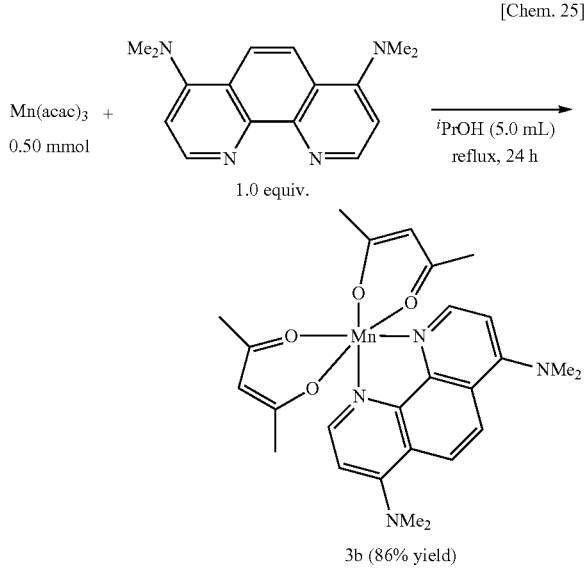

3b (86% yield)

Manganese acetylacetonate [Mn(acac)$_3$] and 1,10-phenanthroline having a substituent at the 4- and 7-positions [ligand (L11)] were allowed to react in isopropyl alcohol (IPA) at a reflux temperature for 24 hours, thereby obtaining a manganese complex [Mn(acac)$_2$(NMe$_2$-Phen)].

X-ray single crystal structure analysis of the obtained manganese complex was performed. The results of the obtained X-ray single crystal structure are shown in FIG. 1. It was confirmed that the obtained manganese complex was composed of two molecules of acetylacetonate and one molecule of 1,10-phenanthroline, and was a manganese divalent complex.

[Example 80] Studies on Addition of Radical Capturing Agent BHT

[Chem. 26]

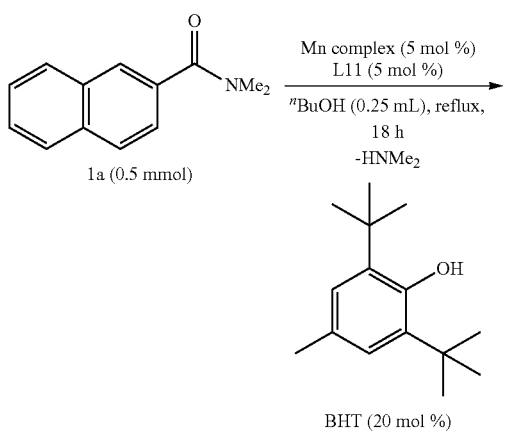

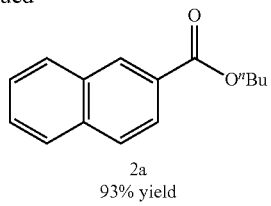

2a
93% yield

A reaction was performed in the same method as Example 1 except that the ligand (L1) in Example 1 was changed to ligand (L11), each of the addition amount of the manganese complex [Mn(acac)$_3$] and the addition amount of the ligand (L11) was 5 mol %, and 20 mol % of dibutylhydroxytoluene (BHT) was used as a radical capturing agent. The yield was measured by an internal standard method using gas chromatography (GC) in the same manner as Example 1, and as a result, the yield was 93%. No decrease in the yield was observed even when BHT was added as the radical capturing agent.

[Synthesis Example 2] Synthesis of Manganese Cubane Complex (1-1) Synthesis of Manganese Precursor ([Mn(acac)(OEt)(OHMe)]$_4$ Manganese Cubane Complex) Cat1a

[Chem. 27]

MnCl$_2$ + Hacac + 2 LiOEt $\xrightarrow[\text{-2 LiCl}]{\text{EtOH, rt, 3 h}}$

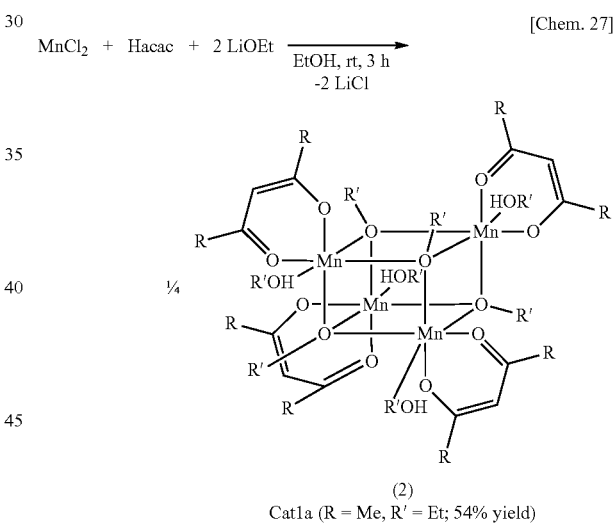

(2)
Cat1a (R = Me, R' = Et; 54% yield)

Hexane (5 mL) was added to lithium (72.1 mg, 10.4 mmol), ethanol (10 mL) was added dropwise, and the reaction was continued until the lithium was completely dissolved. The solvent was distilled off under reduced pressure, and the obtained product was dissolved in ethanol (10 mL) again, and the obtained solution was slowly added to an ethanol solution (10 mL) of manganese chloride (0.629 g, 5.00 mmol) and acetylacetone (Hacac) (530 mL, 5.00 mmol), thereby obtaining a yellow suspension. A yellow solid obtained by stirring the yellow suspension at room temperature for three hours and removing a supernatant was washed with ethanol (1 mL) for four times and was subjected to vacuum drying, thereby obtaining yellow powders (666 mg, 679 mmol, yield of 54%). Recrystallization was performed in a two-layer system of toluene/ethanol. A light yellow solid having a melting point of 282° C. to 290° C. was obtained.

Elemental analysis results: $C_{36}H_{72}O_{16}Mn_4$

Calculated value C, 43.96; H, 7.69

Measured value C, 43.96; H, 7.69

Figure 5:
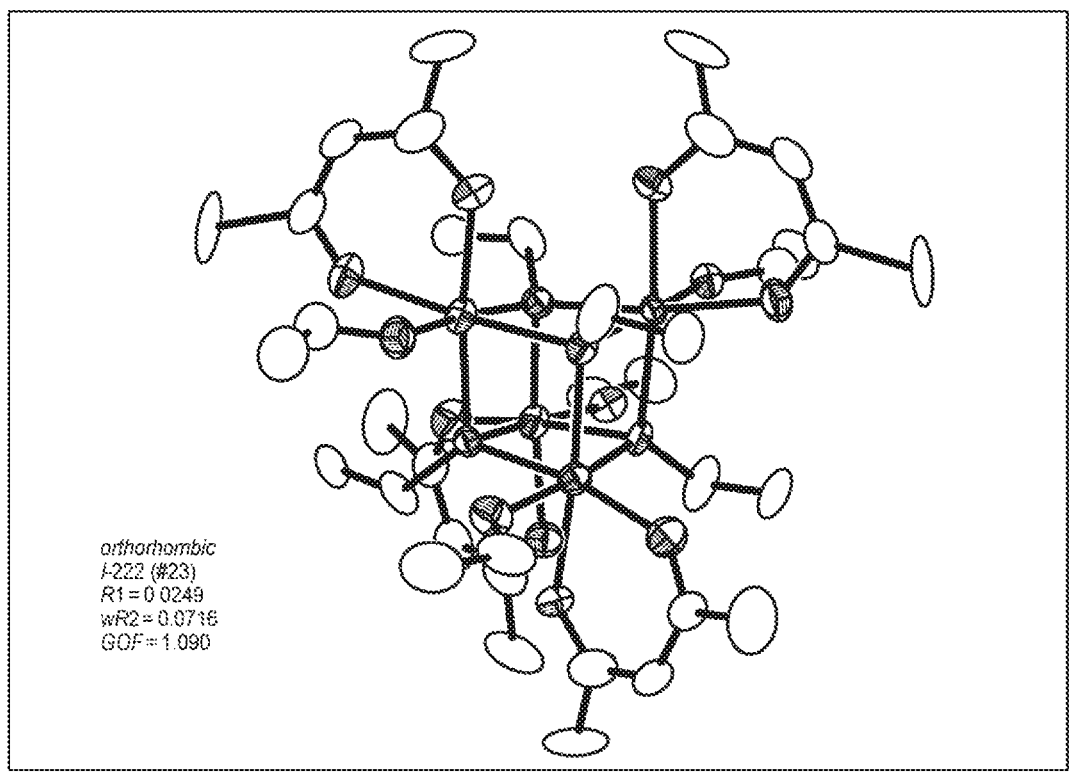
FIG. 5 shows results of X-ray crystal structure analysis of a single crystal obtained in Synthesis Example 2.

The obtained single crystal was subjected to X-ray crystal structure analysis, and the single crystal was confirmed to be a cubane complex Cat1a shown in FIG. 5.

(1-2) Synthesis of Manganese Precursor ([Mn(dpm)(OMe)(MeOH)]$_4$ Manganese Cubane Complex) Cat1b

[Chem. 28]

$$MnCl_2 + Hdpm + 2 KOMe \xrightarrow[-2 LiCl]{MeOH, rt, 3 h}$$

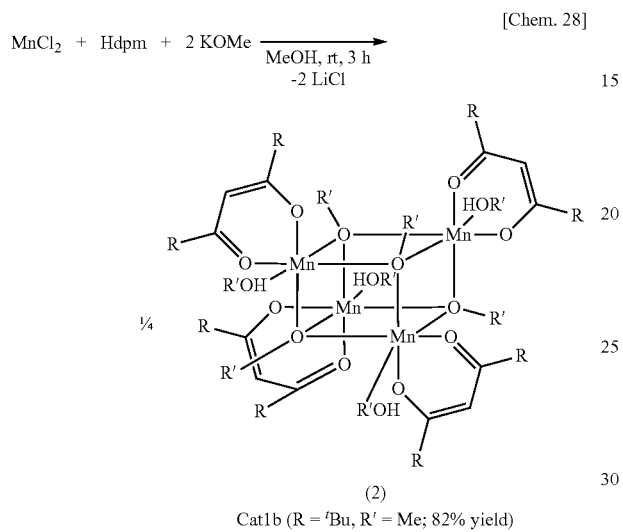

(2)

Cat1b (R = $^t$Bu, R' = Me; 82% yield)

Methanol (5 mL) and dipivaloylmethane (Hdpm) (1.00 mL, 5.00 mmol) were added to manganese chloride (0.629 g, 5.00 mmol), and the manganese chloride was dissolved. A methanol (MeOH) solution (10 mL) of potassium methoxide (KOMe) (0.701 g, 10.0 mmol) was added to the above solution, and then, a yellow precipitate was generated.

Stirring was performed at room temperature for three hours, and a supernatant was removed, thereby obtaining a yellow solid. This solid was extracted with toluene (11 mL) and was subjected to two-layer system recrystallization using methanol, thereby obtaining a yellow crystal (1.234 g, 1.02 mmol, yield of 82%).

[Synthesis Example 3] Isolation of Alkoxide-Crosslinked Binuclear Complex Cat2a

A phenanthroline ligand was added to the cubane complex Cat1a synthesized as described above, and the mixture was heated at 100° C. for 18 hours in toluene. As a result, an alkoxide-crosslinked binuclear complex Cat2a was generated, and a crystal of Cat2a could be obtained.

Cat2a was a dark red solid having a melting point of 230° C. to 234° C.

Elemental analysis results: $C_{38}H_{40}N_4O_6Mn_2$

Calculated value C, 60.16; H, 5.31; N, 7.39

Measured value C, 60.10; H, 5.27; N, 7.14.

Figure 6:
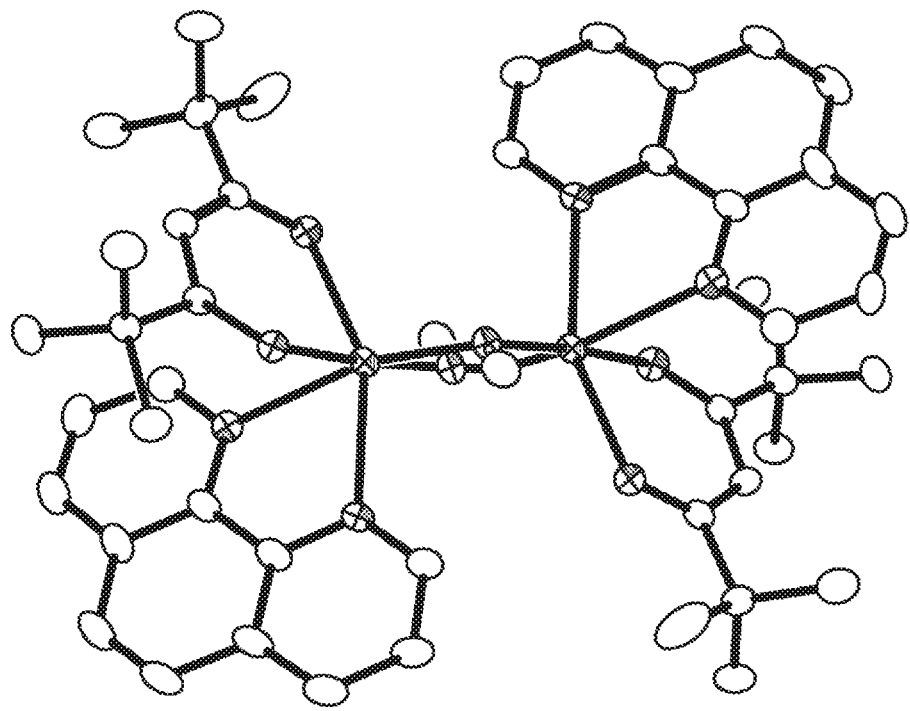
FIG. 6 shows results of X-ray crystal structure analysis of a single crystal obtained in Synthesis Example 3.

The obtained single crystal was subjected to X-ray crystal structure analysis, and the single crystal was confirmed to be Cat2a shown in FIG. 6.

[Chem. 29]

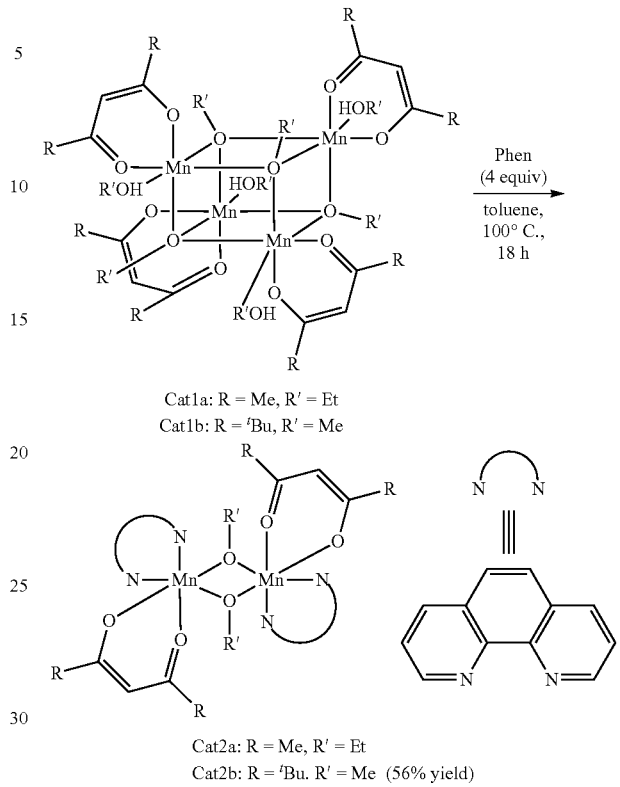

Cat1a: R = Me, R' = Et
Cat1b: R = $^t$Bu, R' = Me

Cat2a: R = Me, R' = Et
Cat2b: R = $^t$Bu, R' = Me (56% yield)

The X-ray crystal structure analysis of the cubane complex Cat1a and the above Cat2a is shown in Table 10.

TABLE 10

| | Cat1a | Cat2a |
|---|---|---|
| CCDC Reference No. | 1865079 | 1865030 |
| empirical formula | $C_{36}H_{72}O_{16}Mn_4$ | $C_{52}H_{54}N_4O_6Mn_2$ |
| formula weight | 980.71 | 940.90 |
| crystal system | orthorhombic | monoclinic |
| space group | I222 (#23) | P2$_1$/c (#14) |
| a, Å | 12.1248(13) | 10.4733(10) |
| b, Å | 14.1447(15) | 20.948(2) |
| c, Å | 14.1468(15) | 10.6581(11) |
| α, deg. | — | — |
| β, deg. | — | 94.542(2) |
| γ, deg. | — | — |
| V, Å$^3$ | 2426.2(4) | 2331.0(4) |
| Z | 2 | 2 |
| Dcalcd, g/cm$^3$ | 1.342 | 1.340 |
| μ [Mo-Kα], cm$^{-1}$ | 10.761 | 5.957 |
| T, K | 113(1) | 113(1) |
| crystal size, mm | 0.23 × 0.23 × 0.23 | 0.10 × 0.10 × 0.05 |
| θrange for data collection (deg.) | 3.60 to 27.50 | 3.004 to 27.311 |
| no. of refections measured | 24753 | 38145 |
| unique data (Rint) | 2786 (0.0177) | 5350 (0.0482) |
| data/restraints/parameters | 2786/0/200 | 5350/0/367 |
| R1 (I > 2.0σ(I)) | 0.0249 | 0.0348 |
| wR2 (I > 2.0σ(I)) | 00716 | 0.0927 |
| R1 (all data) | 0.0255 | 0.0477 |
| wR2 (all data) | 0.0722 | 0.0969 |
| GOF on F$^2$ | 1.090 | 1.071 |
| Δρ, e Å$^{-3}$ | 0.52, −0.28 | 0.56, −0.26 | a) R1 = (Σ||Fo| − |Fc||)/(Σ|Fo|)
b) wR2 = [{Σw(Fo$^2$ − Fc$^2$)$^2$}/{Σw(Fo$^4$)}]$^{1/2}$

[Examples 81 to 88, and Comparative Examples 11 to 13] Conversion Reaction from 2-Naphthoic Acid Amide (1a) to 2-Naphthoic Acid Ester (2a) Using Various Manganese Complexes

[Example 89] Kinetic Analysis Using Isolated Complex Cat2a

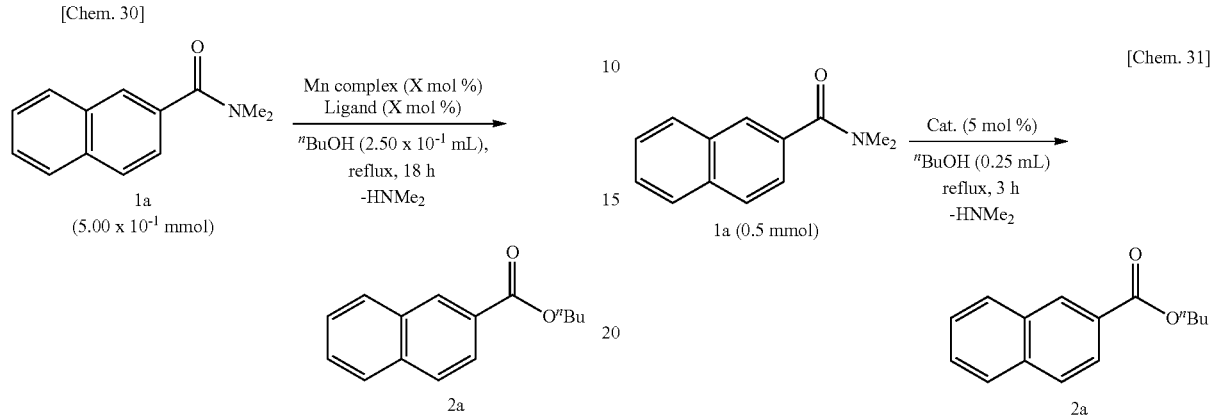

To 0.50 mmol of 2-naphthoic acid amide (1a) and 0.25 mL of 1-butanol, a metal precursor in an amount shown in Table 11 and a ligand in an amount shown in Table 11 were added, and the reaction was performed at a reflux temperature for 18 hours while discharging dimethylamine as a by-product from a reaction system.

In Comparative Example 13, 1 mol % of NaOMe was added instead of the addition of a metal precursor and a ligand.

The yield was determined by gas chromatography (GC) analysis using dodecane as an internal standard substance. Reaction results of Examples 81 to 88 and Comparative Examples 11 to 13 are shown in Table 11.

TABLE 11

|  |  | Metal precursors | Ligands | Addition amount x [mol %] | Yield [%] |
|---|---|---|---|---|---|
| Examples | 81 | Cat1a | L11 | 1 | 90 |
|  | 82 | Cat1b | L11 | 1 | 79 |
|  | 83 | Cat1b | L8 | 1 | 50 |
|  | 84 | Mn(acac)$_2$ | L11 | 1 | 85 |
|  | 85 | Mn(dpm)$_2$ | L11 | 1 | 57 |
|  | 86 | Mn(hfac)$_2$ | L11 | 1 | 52 |
|  | 87 | Mn(OAc)$_2$ | L11 | 1 | 57 |
|  | 88 | Cat1a | L11 | 2 | >99 |
| Comparative Examples | 11 | [Mn(dpm)(OMe)(Phen)]$_2$ | — | 1 | 45 |
|  | 12 | Cat1a | — | 1 | 22 |
|  | 13 | — | — | 1 (NaOMe) | — |

A product was obtained with a GC yield of 99% or more in the case where a cubane complex Cat1a [Mn(acac)(OEt)(EtOH)]$_4$ was used as a catalyst or in the case where 1 mol % (manganese standard) of catalyst was used. The activity of these showed values higher than the activity when the mononuclear complex Mn(dpm)$_2$ was used as a metal precursor.

In the case where a phenanthroline ligand was not added to the cubane complex Cat1a [Mn(acac)(OEt)(EtOH)]$_4$, the reaction did not proceed (Comparative Example 12).

In the case of the reaction in which 1 mol % of NaOMe was added instead of the addition of a metal precursor and a ligand, the reaction did not proceed (Comparative Example 13). It was found that the reactivity was high in the case where the cubane complex was used as a metal precursor.

The alkoxide-crosslinked binuclear complex Cat2a obtained in Synthesis Example 3 was used to study the esterification reaction.

Specifically, to 0.5 mmol of 2-naphthoic acid amide (1a) and 0.25 mL of 1-butanol, (i) 5 mol % of Mn(acac)$_3$ and 5 mol % of Me$_2$N-Phen, (ii) 5 mol % of Cat2a, (iii) mol % of Cat2a and 5 mol % of potassium 4-tolylbenzyl alkoxide (KOCH$_2$C$_6$H$_4$CH$_3$-4), or (iv) 5 mol % of potassium 4-tolylbenzyl alkoxide (KOCH$_2$C$_6$H$_4$CH$_3$-4) were added, and the reaction was performed at a reflux temperature for three hours while discharging dimethylamine as a by-product from a reaction system.

The yield of 2-naphthoic acid ester (2a) at that time was measured by an internal standard method using dodecane and gas chromatography (GC). The reaction results of (i) to (iv) are shown in the above chemical formula.

Although the reaction proceeded only with the alkoxide-crosslinked binuclear complex Cat2a (ii), the yield was 87% by further adding potassium 4-tolylbenzyl alkoxide (KOCH$_2$C$_6$H$_4$CH$_3$-4) (iii). However, the yield was 12%, which was low, when only potassium 4-tolylbenzyl alkoxide was added (iv), so that the effect of adding potassium 4-tolylbenzyl alkoxide was confirmed.

1 equivalent of potassium alkoxide salt, which was an additive, was added to a catalyst, and then, it was found that catalytic activity was further improved and the catalyst was not deactivated.

Therefore, the kinetic analysis was performed in accordance with a kinetic analysis method for a catalytic reaction described in Angew. Chem., Int. Ed. 55 (2016) p. 16084 using the alkoxide-crosslinked binuclear complex Cat2a.

To 2-naphthoic acid amide (1a) (398.5 mg, 2 mmol, 2.00 mol/L), the alkoxide-crosslinked binuclear complex Cat2a (0.06 mol/L), and a potassium salt (0.06 mol/L), 1.0 mL of 1-butanol was added, and the reaction was performed at a reflux temperature of 145° C. while discharging dimethylamine as a by-product from a reaction system. Temporal changes of the yield of 2-naphthoic acid ester (2a) at that time were measured by using gas chromatography (GC).

Figure 2:
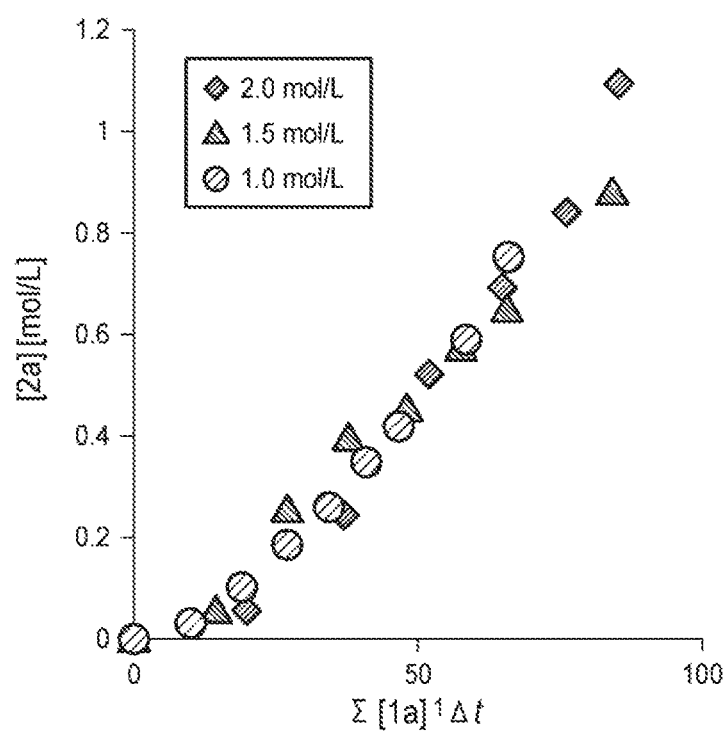
FIG. 2 shows results of reaction rate analysis in Example 89 by plotting concentrations [2a] of 2-naphthoic acid ester (2a) relative to a horizontal axis represented by the sum of products of $[1a]^\alpha$ and $\Delta t$ in which $\Delta t$ ($=t_i-t_{i-1}$) is a measurement interval, and $[1a]^\alpha$ is $\alpha$ power of an average value of concentrations of 2-naphthoic acid amide (1a) from the time point $t_{i-1}$ to $t_i$.

Reactions were performed similarly in the cases where concentrations of 2-naphthoic acid amide (1a) as a raw material were 1.00 mol/L and 1.50 mol/L. Concentrations [2a] of 2-naphthoic acid ester (2a) were plotted relative to a horizontal axis represented by the sum of products of $[1a]^\alpha$ and $\Delta t$ in which $\Delta t$ $(=t_i-t_{i-1})$ is a measurement interval, and $[1a]^\alpha$ is a power of an average value of concentrations of 2-naphthoic acid amide (1a) from the time point $t_{i-1}$ to $t_i$. Since the plots at three concentrations overlapped when $\alpha=1$ it was found that the reaction rate was proportional to 1 power of the concentration of 2-naphthoic acid amide (1a) (FIG. 2).

To 2-naphthoic acid amide (1a) (398.5 mg, 2 mmol, 2.00 mol/L), the alkoxide-crosslinked binuclear complex Cat2a (0.06 mol/L), and a potassium salt, 1.0 mL of 1-butanol was added, and the reaction was performed at a reflux temperature of 145° C. while discharging dimethylamine as a by-product from a reaction system. Temporal changes of the concentration [1a] of 2-naphthoic acid amide (1a), which was a starting material, at that time were measured by using gas chromatography (GC). The measurement was similarly performed in the reaction system in which catalyst amounts of the alkoxide-crosslinked binuclear complex Cat2a were different therefrom, i.e. the addition amount thereof being 0.10 mol/L and 0.14 mol/L respectively.

Figure 3:
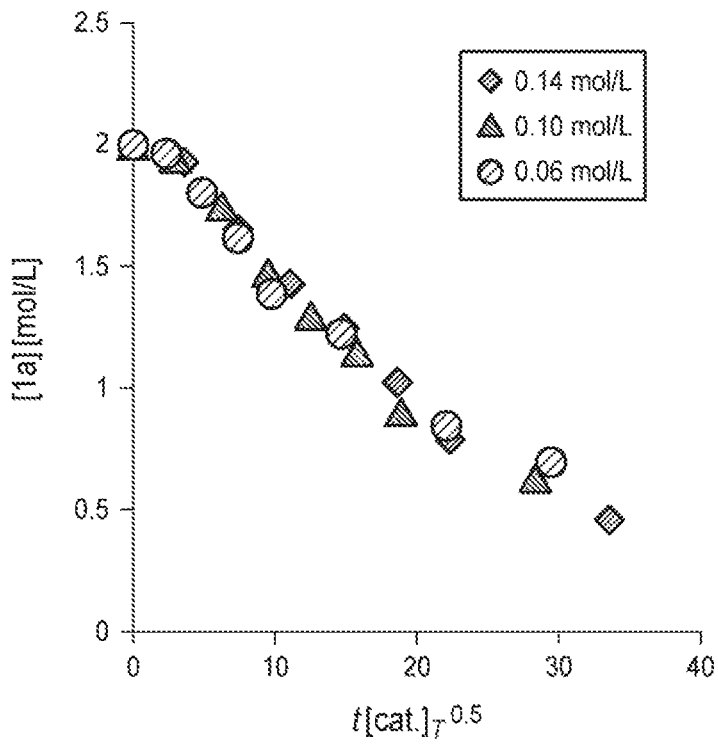
FIG. 3 shows results of reaction rate analysis in Example 89 by showing a normalized time $t[cat.]_T^n$ ($[cat.]_T$=concentration of catalyst) using a concentration of a catalyst on a horizontal axis and plotting temporal changes of concentrations [1a] of 2-naphthoic acid amide (1a), which is a starting material, on a vertical axis.

The reaction rate analysis was performed by showing a normalized time $t[cat.]_T^n$ ($[cat.]_T$=concentration of catalyst) using a concentration of a catalyst on a horizontal axis and plotting temporal changes of concentrations [1a] of 2-naphthoic acid amide (1a), which was a starting material, on a vertical axis (FIG. 3). As a result, the plots at three concentrations overlapped when n=0.5, so that it was found that the reaction rate was proportional to 0.5 power of the concentration of the catalyst.

Based on the above two results, it was found that the reaction rate v can be expressed by the concentration [1a] of 2-naphthoic acid amide (1a) as a raw material and the concentration [6a] of the catalyst.

$$v=k_{obs}[1a]^1[6a]^{0.5}$$

Next, the velocity obeys "$k_{obs}$" in the above formula was determined.

Figure 4:
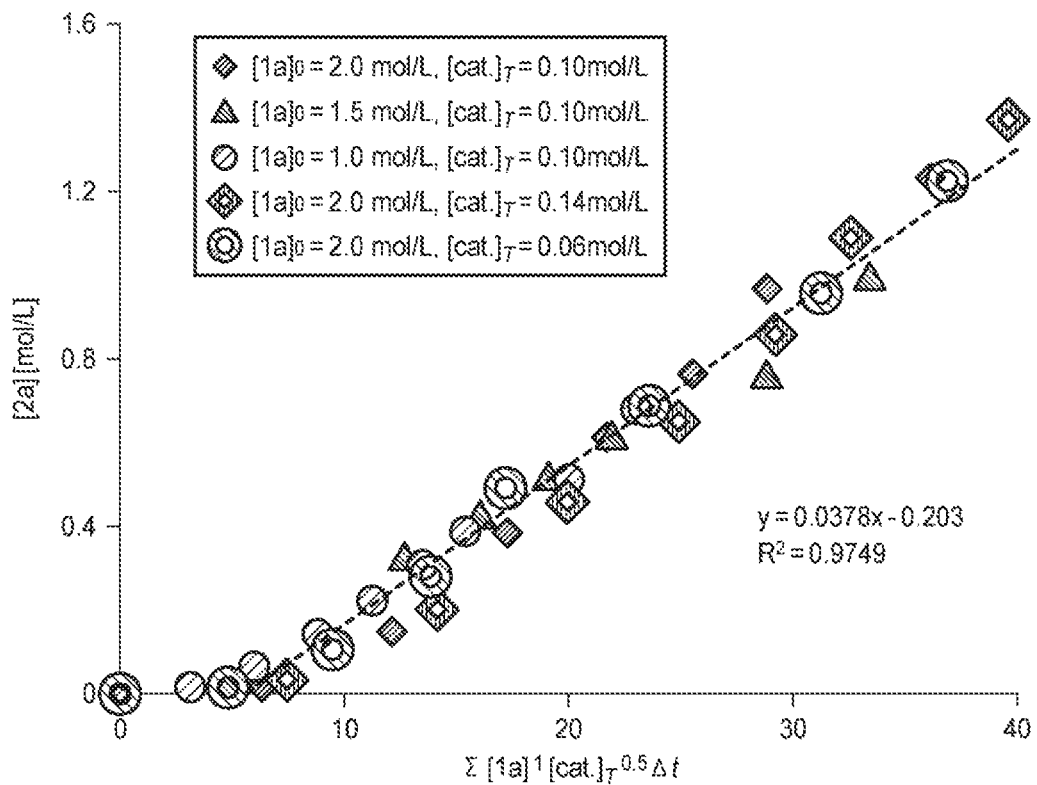
FIG. 4 shows results of reaction rate analysis in Example 89 by a normalizing time scale by using $[1a]^1 \cdot [6a]^{0.5}$ which is a power value obtained by multiplying 1 of a concentration of 2-naphthoic acid amide (1a) as a raw material with 0.5 power value of a concentration of a catalyst on a horizontal axis, and plotting a concentration [2a] of 2-naphthoic acid ester (2a) on a vertical axis.

The time was normalized by using a power value $[1a]^1 \cdot [6a]^{0.5}$ obtained by multiplying 1 of a concentration of 2-naphthoic acid amide (1a) as a raw material with 0.5 power value of a concentration of a catalyst on a horizontal axis, and concentrations [2a] of 2-naphthoic acid ester (2a) were plotted on a vertical axis (FIG. 4).

It was found that the concentrations [2a] were plotted on the same line under all reaction conditions. The reaction rate constant was calculated from this inclination, and then, the velocity obeys "$k_{obs}$" was obtained as $4.5 \times 10^{-1}$ mol/L-0.5 min$^{-1}$.

$R^2$ in FIG. 4 represents a decision coefficient. The closer the value is to 1, the higher the linearity is.

In addition, $[1a]_0$ in FIG. 4 represents an initial concentration of 2-naphthoic acid amide (1a).

A reaction mechanism was considered based on the above analysis results. The reaction rate depends on the 0.5 power of the concentration of the catalyst, so that the manganese complex exists as an inert μ-oxo-dimer complex in a reaction system, and the μ-oxo-dimer complex is considered to be in equilibrium with a mononuclear complex which is an active species. That is, it became clear that the μ-oxo-dimer complex is involved in the reaction of the present invention.

[Examples 90 to 93] Transesterification Reaction Using Tertiary Alcohols and Phenol Derivatives

[Chem. 32]

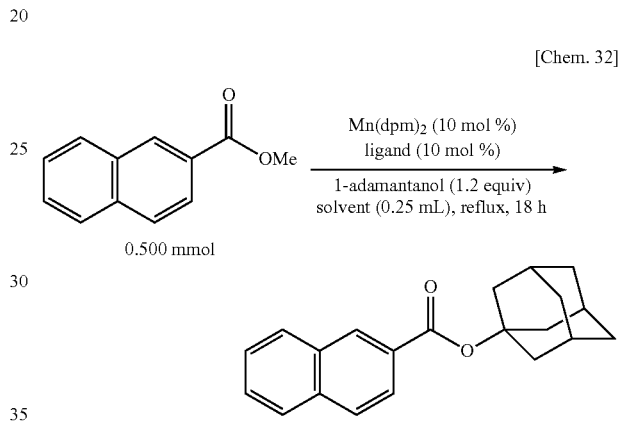

To 2-naphthoic acid methyl ester (0.5 mmol), 1-adamantanol (1.2 equivalents), and 0.25 mL of a solvent shown in Table 12, manganese dipivaloylmethanate (Mn(dpm)$_2$) (10 mol %) and a ligand shown in Table 12 were added as a catalyst, and the reaction was performed at a reflux temperature for 18 hours, and studies on the catalytic transesterification reaction was performed.

The yield of the product at that time was measured by an internal standard method using dodecane and gas chromatography (GC). The conversion rates in Table 12 were determined by using $^1$H-NMR with triphenylmethane as an internal standard. The reaction results of Examples 90 to 93 are shown in Table 12.

TABLE 12

| Examples | Ligands | Solvents | Conversion rates [%] | Yield [%] |
|---|---|---|---|---|
| 90 | L1 | Toluene | 75 | 67 |
| 91 | L1 | CPME | 89 | 82 |
| 92 | L8 | CPME | 84 | 72 |
| 93 | L11 | CPME | 99 | 92 |

The yield in the case where cyclopentyl methyl ether (CPME) was used was better than that in the case where toluene was used as a solvent (Examples 91 to 93).

In the case where CPME was used as the solvent and 1,10-phenanthroline (ligand (L8)) was used, a target product was obtained with a yield which is slightly lower than the yield in the case where 2,2'-bipyridine [ligand (L1)] was used (Example 92).

In the case where 4,7-bis(dimethylamino)-1,10-phenanthroline (NMe$_2$-Phen) [ligand (L11)] having a high electron donating ability was used, the raw materials were almost consumed and the target product was obtained with a very high yield (Example 93).

[Synthesis Example 4] Synthesis of [Ni(dpm)(OMe)(MeOH)]$_4$ (Cat3a)

Figure 7:
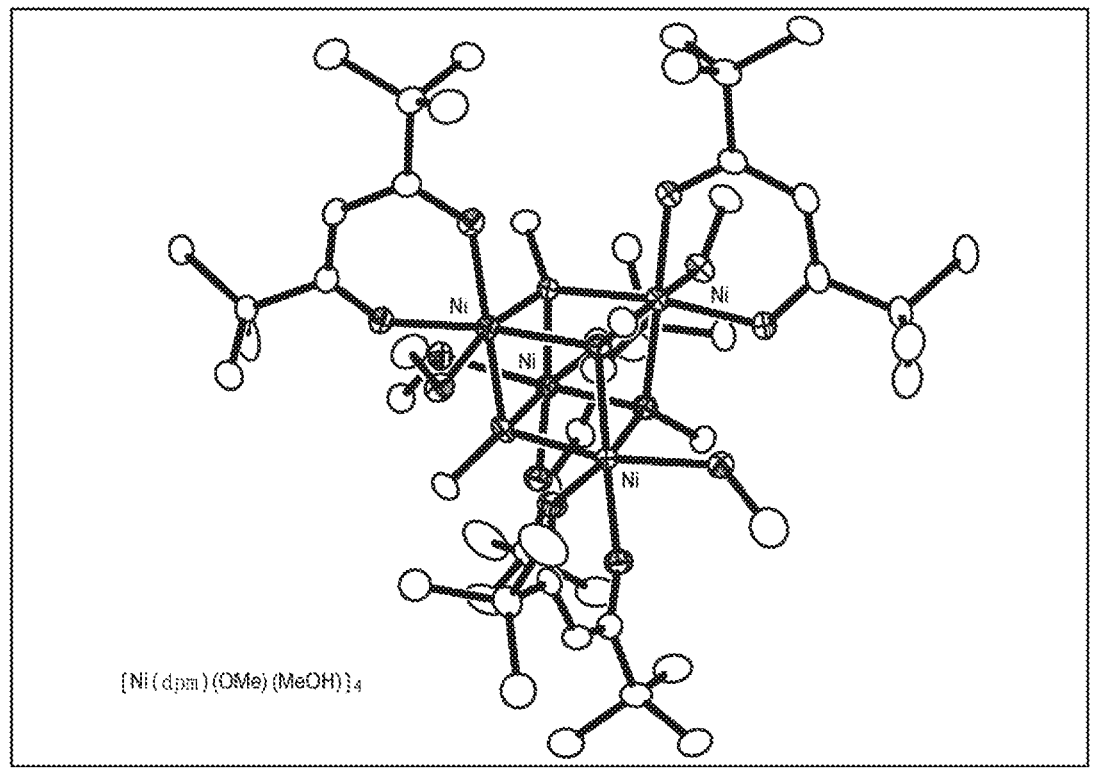
FIG. 7 shows results of X-ray crystal structure analysis of a single crystal obtained in Synthesis Example 4.

Nickel chloride anhydride (389 mg, 3.00 mmol) was weighed and put into a Schlenk bottle, dipivaloylmethane (0.620 mL, 3.00 mmol) was added to the Schlenk bottle under argon, and the mixture was suspended in 15 mL of methanol. Potassium methoxide (463 mg, 6.00 mmol) was weighed and put into another Schlenk bottle, and was dissolved in 5 mL of methanol. This solution was added dropwise to the nickel chloride suspension, and then the mixed solution was stirred at room temperature for one night under the argon atmosphere. Thereafter, a yellow-green precipitate was recovered by filtration and dried under reduced pressure. Thereafter, the dried precipitate was extracted with 10 mL of toluene, and then, 20 mL of methanol was added, followed by bilayer recrystallization, thereby obtaining 645 mg of a yellow-green crystal with a yield of 70%. The obtained single crystal was subjected to X-ray crystal structure analysis, and the single crystal was confirmed to be Cat3a shown in FIG. 7.

[Synthesis Example 5] Synthesis of [Zn(dpm)(OMe)(MeOH)]$_4$ (Cat4a)

Figure 8:
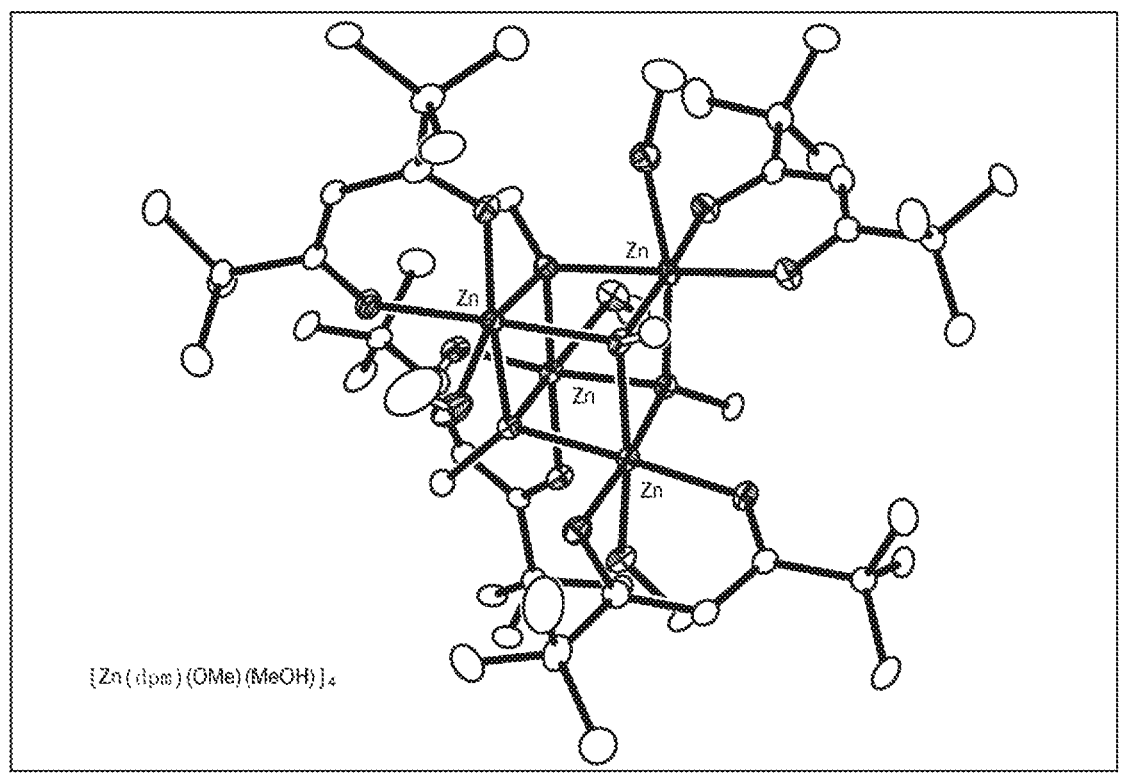
FIG. 8 shows results of X-ray crystal structure analysis of a single crystal obtained in Synthesis Example 5.

Potassium methoxide (463 mg, 6.00 mmol) was weighed and put into a Schlenk bottle, and was dissolved in 5 mL of methanol. Zinc chloride anhydride (409 mg, 3.00 mmol) was weighed and put into another Schlenk bottle, 2,2,6,6-tetramethyl-3,5-heptanedione (0.620 mL, 3.00 mmol) was added to the Schlenk bottle under argon, and the mixture was dissolved in 5 mL of methanol. This solution was added dropwise to the other solution, and then, the mixed solution was stirred at room temperature for three hours under the argon atmosphere. Thereafter, a white precipitate was recovered by filtration and dried under reduced pressure. Thereafter, the dried precipitate was extracted with 3 mL of toluene, and then, 15 mL of methanol was added, followed by bilayer recrystallization, thereby obtaining 546 mg of a colorless crystal with a yield of 58%. The obtained single crystal was subjected to X-ray crystal structure analysis, and the single crystal was confirmed to be Cat4a shown in FIG. 8.

[Example 94] Conversion Reaction from 2-Naphthoic Acid Amide (1a) to 2-Naphthoic Acid Ester (2a)

A reaction was performed in the same manner as Example 1 except that the metal precursor was changed to the nickel complex Cat3a, and 10 mol % of 2,2'-bibipyridine [ligand (L1)] was changed to 5 mol % of 1,10-phenanthroline [ligand (L8)].

The yield of the product at that time was measured by an internal standard method using dodecane and gas chromatography (GC). The yield was 30%.

[Examples 95 and 96] Conversion Reaction from 2-Naphthoic Acid Amide (1a) to 2-Naphthoic Acid Ester (2a)

[Chem. 33]

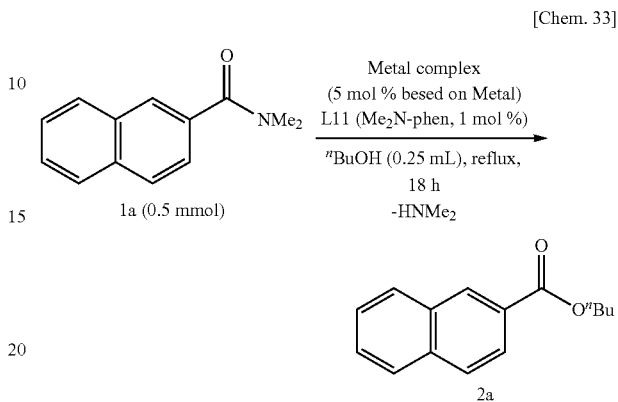

To 0.50 mmol of 2-naphthoic acid amide (1a) and 0.25 mL of 1-butanol, 1 mol % of a metal complex shown in Table 13 and 5 mol % of a ligand (L11) were added, and the reaction was performed at a reflux temperature for 18 hours while discharging dimethylamine as a by-product from a reaction system.

The yield of 2-naphthoic acid ester (2a) at that time was measured by an internal standard method using dodecane and gas chromatography (GC). The reaction results of Examples 95 and 96 are shown in Table 13.

TABLE 13

| Examples | Metal precursors | Yield [%] |
|---|---|---|
| 95 | Cat1b | 80 |
| 96 | Cat3a | 76 |

In the case where the ligand (L11) was used, high catalytic activity was exhibited even if the catalyst amount was reduced to 1 mol %. High catalytic activity was also exhibited in the case where the nickel complex Cat3a was used, which is similar to the case where a manganese cubane complex Cat1b was used as a metal precursor.

[Examples 97 to 101] Conversion Reaction from 2-Naphthoic Acid Amide (1a) to 2-Naphthoic Acid Ester (2a)

[Chem. 34]

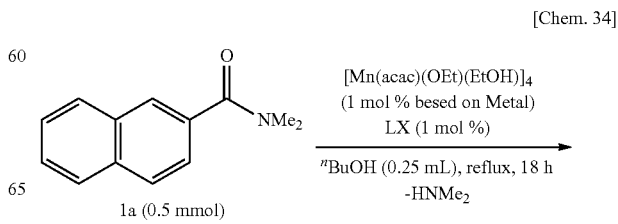

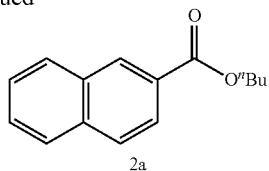

2a

The conversion reaction from 2-naphthoic acid amide (1a) to 2-naphthoic acid ester (2a) was performed by using a cubane complex Cat1a [Mn(acac)(OEt)(EtOH)]$_4$ in an amount of 1 mol % (manganese standard) as a metal precursor.

Specifically, 1 mol % of the manganese cubane complex Cat1a and 1 mol % of the ligand shown in Table 14 were added to 0.50 mmol of 2-naphthoic acid amide (a) and 0.25 mL of 1-butanol, and the reaction was performed at a reflux temperature for 18 hours while discharging dimethylamine as a by-product from a reaction system.

The yield of 2-naphthoic acid ester (2a) at that time was measured by an internal standard method using dodecane and gas chromatography (GC). The reaction results of Examples 97 to 101 are shown in Table 14.

TABLE 14

| Examples | Ligands | Yield [%] |
|---|---|---|
| 97 | L8 | 36 |
| 98 | L9 | 54 |
| 99 | L10 | 67 |
| 100 | L11 | 90 |
| 101 | L12 | 68 |

[Examples 102 to 112] Conversion Reaction from Amide Compound to Ester Compound

The conversion reaction from 2-naphthoic acid amide to 2-naphthoic acid ester was performed by using a cubane complex Cat1a [Mn(acac)(OEt)(EtOH)]$_4$ in an amount of 2 mol % (manganese standard) as a metal precursor.

Specifically, reactions were performed in the same method as Example 97 except that the amide as a raw material (2-naphthoic acid amide (1a)) in Example 97 was changed to the above compound 1 having a substituent R shown in Table 15, the metal precursor was changed to the cubane complex Cat1a, and each of the addition amount of the metal precursor and the addition amount of the ligand was changed to 2 mol %.

The yield of 2-naphthoic acid ester (2a) at that time was measured. The reaction results of Examples 102 to 112 are shown in Table 15. Yield indicates an isolation yield.

TABLE 15

| Examples | R | Yield [%] |
|---|---|---|
| 102 | Phenyl | 78 |
| 103 | p-Tolyl | 77 |
| 104 | p-OMeC$_6$H$_4$ | 65 |
| 105 | p-CF$_3$C$_6$H$_4$ | 84 |
| 106 | p-CNC$_6$H$_4$ | 86 |
| 107 | p-BrC$_6$H$_4$ | 78 |
| 108 | P-ClC$_6$H$_4$ | 92 |
| 109 | m-CF$_3$C$_6$H$_4$ | 77 |
| 110 | P-IC$_6$H$_4$ | 86 |
| 111 | 4-pyridyl | 98 |
| 112 | 2-furyl | 88 |

[Examples 113 to 17] Conversion Reaction from 2-Naphthoic Acid Amide (1a) to 2-Naphthoic Acid Ester (2a)

The conversion reaction from 2-naphthoic acid amide (1a) to 2-naphthoic acid ester was performed by using a cubane complex Cat1a [Mn(acac)(OEt)(EtOH)]$_4$ in an amount of 1 mol % (manganese standard) as a metal precursor.

Specifically, the conversion reaction from 2-naphthoic acid amide (a) to 2-naphthoic acid ester (2a) was performed in the same manner as Example 81 except that the used alcohols were changed as shown in Table 16.

The yield of 2-naphthoic acid ester (2a) at that time was measured. The reaction results of Examples 113 to 117 are shown in Table 15. Yield indicates an isolation yield.

TABLE 16

| Examples | Alcohols | Yield [%] |
|---|---|---|
| 113 | HO~~~ | 93 |
| 114 | (2-pentanol, OH on C2) | 69 |
| 115 | (4-heptanol, OH on C4) | 78 |
| 116 | tert-butanol | 51 |
| 117 | HO-CH$_2$-p-Tol | 92 |

[Examples 118 to 124] Conversion Reaction from Amide Compound to 2-Naphthoic Acid Ester (2a)

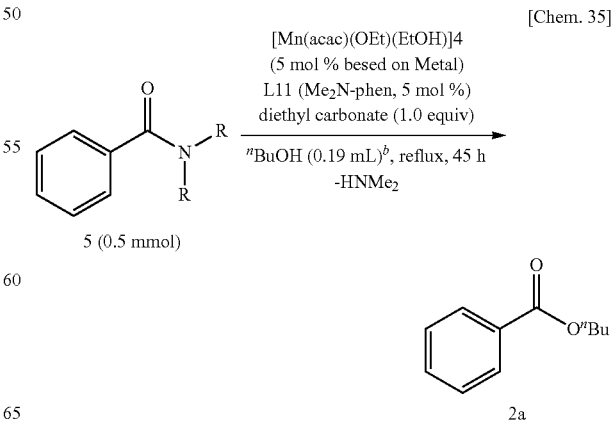

The conversion reaction from an amide compound to 2-naphthoic acid ester (2a) was performed by using a cubane complex Cat1a [Mn(acac)(OEt)(EtOH)]$_4$ in an amount of 5 mol % (manganese standard) as a metal precursor.

Specifically, the conversion reaction from an amide compound to 2-naphthoic acid ester (2a) was performed in the same manner as Example 81 except that the amide as a raw material (2-naphthoic acid amide (1a)) in Example 81 was changed to substances having a variety of substituents on a nitrogen atom as shown in Table 17.

The yield was measured by an internal standard method using gas chromatography (GC) in the same manner as Example 1. The reaction results of Examples 118 to 124 are shown in Table 17.

In Example 118, an isolation yield was also measured.

TABLE 17

| Examples | Amide as raw material | Yield [%] |
|---|---|---|
| 118 | ![benzoyl piperidine] | 81 (Isolation yield 77) |
| 119 | ![benzoyl morpholine] | 88 |
| 120 | ![N-methyl-N-phenyl benzamide] | 93 |
| 121 | ![benzoyl pyrrole] | 92 |
| 122 | ![N-methyl benzamide] | 60 |
| 123 | ![N-Q benzamide] | 83 |
| 124 | ![benzamide NH2] | 82 |

Q in Table 17 represents the following substituents.

[Chem. 36]

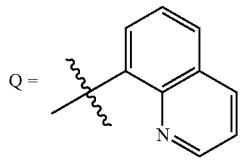

[Examples 125 to 126] Conversion Reaction from 2-Naphthoic Acid Amide (1a) to 2-Naphthoic Acid Ester (2a)

[Chem. 37]

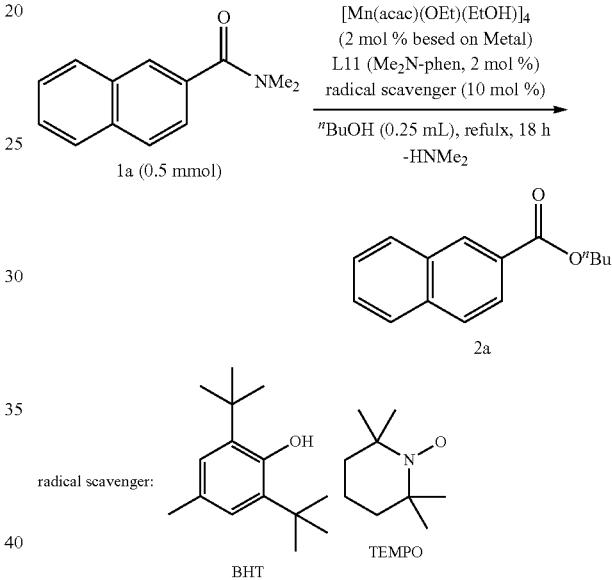

The conversion reaction from 2-naphthoic acid amide (1a) to 2-naphthoic acid ester (2a) was performed by using a cubane complex Cat1a [Mn(acac)(OEt)(EtOH)]$_4$ in an amount of 2 mol % (manganese standard) as a metal precursor.

Specifically, 1 mol % of the manganese cubane complex Cat1a, 2 mol % of the ligand (L11), and 10 mol % of the radical capturing agent (BHT or 2,2,6,6-tetramethylpiperidine 1-oxyl (TEMPO)) were added to 0.50 mmol of 2-naphthoic acid amide (1a) and 0.25 mL of 1-butanol, and the reaction was performed at a reflux temperature for 18 hours while discharging dimethylamine as a by-product from a reaction system.

The yield of 2-naphthoic acid ester (2a) at that time was measured by an internal standard method using dodecane and gas chromatography (GC).

The yield in the case of using BHT (Example 125) was 73%, and the yield in the case of using TEMPO (Example 126) was 83%

No decrease in the yield was observed even when the radical capturing agent was added. From this result, it was clear that the present reaction is not caused by a radical reaction.

[Example 127] Transesterification Reaction Using Tertiary Alcohols and Phenol Derivatives

[Chem. 38]

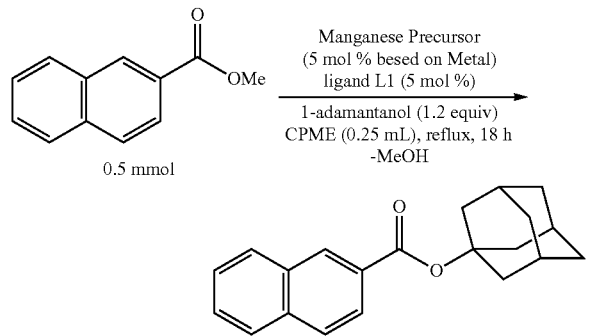

Similar to Example 125, mol % of the manganese precursor Cat1b [Mn(dpm)(OMe)(MeOH)]$_4$, which was prepared in advance, and 5 mol % of 2,2'-bipyridine (L1) were added to 0.5 mmol of 2-naphthoic acid methyl ester and 0.5 mmol of 1-adamantanol in the tertiary alcohols, and the transesterification reaction was performed in a solvent. CPME (0.25 mL) was used as the solvent. The yield was measured by an internal standard method using gas chromatography (GC) in the same manner as Example 1.

The yield was 51%.

The yield in the case where CPME was used was better than the yield in the case where toluene was used as a solvent.

As a comparison, a reaction was performed without adding a manganese precursor, and then, the reaction hardly proceeded (yield: 2%). In addition, the reaction did not occur at all in the case where the manganese chloride hydrate was used as a manganese precursor.

[Example 128] Transesterification Reaction Using Tertiary Alcohols and Phenol Derivatives

[Chem. 39]

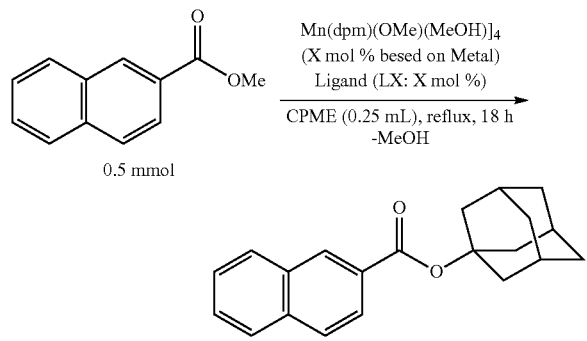

According to Example 127, X mol % of the manganese precursor Cat1b [Mn(dpm)(OMe)(MeOH)]$_4$, which was prepared in advance, and X mol % of a variety of ligands (L6, L11, L12, L20, L22, L26, L30, L31 or L32) shown below were added to 0.5 mmol of 2-naphthoic acid methyl ester and 0.5 mmol of 1-adamantanol in the tertiary alcohols, and the transesterification reaction was performed in a solvent (solvent: CPME). The yield was measured by an internal standard method using gas chromatography (GC) in the same manner as Example 1.

The kinds and addition amounts (X mol %) of the ligands and the yields are shown below.

[Chem. 40]

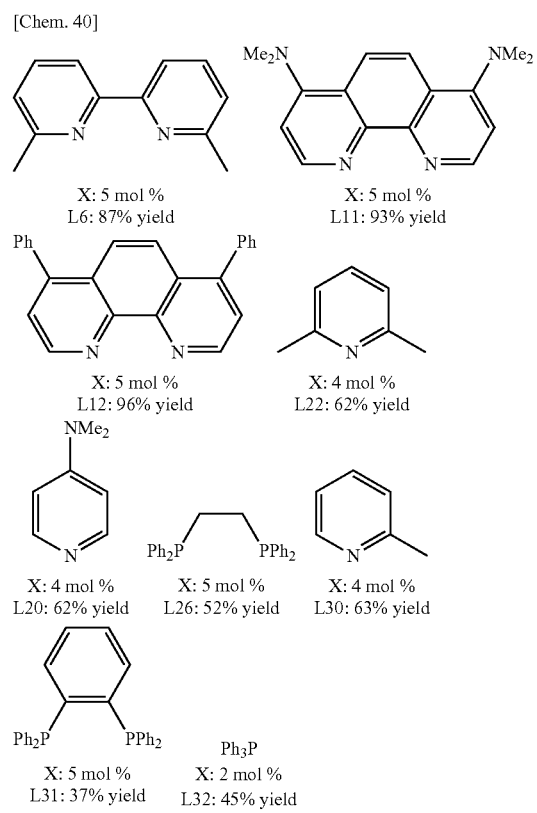

Although the present invention is described in detail using specific embodiments, it will be apparent to those skilled in the art that various modifications and variations are possible without departing from the spirit and scope of the present invention. This application is based on Japanese Patent Application No. 2018-035579 filed on Feb. 28, 2018 and Japanese Patent Application No. 2018-115565 filed on Jun. 18, 2018, contents of which are incorporated herein by reference.

INDUSTRIAL APPLICABILITY

An efficient conversion reaction of tertiary amide compounds to ester compounds can be performed by using a fourth period transition metal complex in the present invention as a catalyst. In addition, a tertiary alcohol ester with a large steric hindrance that was hardly subjected to a transesterification reaction in the related art can be synthesized from the amide compounds.

As a result, the reaction can be performed with good environmental friendliness, operability, and economic efficiency. The reaction of the present invention using the complex of the present invention can be applied to a method for producing pharmaceutical intermediates or agrochemical intermediates, functional materials, structural materials, or the like through the use of it as a protecting group for a carbonyl group or an orientation group.

The invention claimed is:

1. A fourth period transition metal complex, which is obtained by a reaction of a precursor having a fourth period transition metal with a nitrogen-containing compound in the presence of an alcohol or alkoxide,
wherein the fourth period transition metal is selected from the group consisting of scandium (Sc), titanium (Ti), vanadium (V), chromium (Cr), manganese (Mn), cobalt (Co), nickel (Ni), and copper (Cu), and
the nitrogen-containing compound is bipyridine which optionally has substituent(s) or 1,10-phenanthroline which optionally has substituent(s).

2. The fourth period transition metal complex according to claim 1,
wherein the precursor is a metal complex having a ligand selected from the group consisting of beta-diketonates, beta-diketoiminates, and beta-diketiminates, or a carboxylate of the fourth period transition metal.

3. A μ-oxo-dimer complex of the following general formula (1),

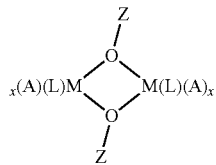

(1)

wherein M represents a fourth period transition metal,
A represents a carboxylic acid residue, a beta-diketonate, a beta-diketoiminate, or a beta-diketiminate,
in the case where A represents the carboxylic acid residue, x represents 2, and in the case where A represents the beta-diketonate, beta-diketoiminate, or beta-diketiminate, x represents 1,
L represents a nitrogen-containing compound or a phosphorus-containing compound, and
Z represents a lower alkyl group which optionally has substituent(s), a lower alkoxy group which optionally has substituent(s), a lower alkenyl group which optionally has substituent(s), a lower alkynyl group which optionally has substituent(s), a halo-lower alkyl group which optionally has substituent(s), a halo-lower alkenyl group which optionally has substituent(s), a halo-lower alkynyl group which optionally has substituent(s), a cyclic hydrocarbon group which optionally has substituent(s), or a heterocyclic group which optionally has substituent(s),
the μ-oxo-dimer complex being obtained by a reaction of a metal complex having a ligand selected from the group consisting of beta-diketonates, beta-diketoiminates, and beta-diketiminates, or a carboxylate of a fourth period transition metal, with a nitrogen-containing compound or phosphorus-containing compound, which are added thereto, in the presence of an alcohol or alkoxide.

* * * * *